US012610901B2

(12) United States Patent
Montoro Ponsoda et al.

(10) Patent No.: US 12,610,901 B2
(45) Date of Patent: Apr. 28, 2026

(54) TOMATO PLANT HAVING IMPROVED INSECT RESISTANCE

(71) Applicant: Enza Zaden Beheer B.V., Enkhuizen (NL)

(72) Inventors: Teresa Maria Montoro Ponsoda, Enkhuizen (NL); Jan-Willem De Kraker, Enkhuizen (NL); Ilona Gertruida Maria Broersen, Enkhuizen (NL); Ilja Roobeek, Enkhuizen (NL); Marieke Ykema, Enkhuizen (NL); Fausto Rodriguez Sánchez, Enkhuizen (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 216 days.

(21) Appl. No.: 18/283,629

(22) PCT Filed: Mar. 24, 2021

(86) PCT No.: PCT/EP2021/057590
§ 371 (c)(1),
(2) Date: Sep. 22, 2023

(87) PCT Pub. No.: WO2022/199812
PCT Pub. Date: Sep. 29, 2022

(65) Prior Publication Data
US 2024/0090397 A1 Mar. 21, 2024

(51) Int. Cl.
*A01H 6/82* (2018.01)
*A01H 1/00* (2006.01)
*C12N 15/82* (2006.01)

(52) U.S. Cl.
CPC ............. *A01H 1/127* (2021.01); *A01H 6/825* (2018.05)

(58) Field of Classification Search
None
See application file for complete search history.

(56) References Cited

U.S. PATENT DOCUMENTS 11,492,634 B2 * 11/2022 Solleveld ............. C12Q 1/6895

FOREIGN PATENT DOCUMENTS

CN 111662366 A 9/2020
WO WO-2018115395 A1 * 6/2018 ............... A01H 6/82

OTHER PUBLICATIONS

Schilmiller, Anthony L., Amanda L. Charbonneau, and Robert L. Last. "Identification of a BAHD acetyltransferase that produces protective acyl sugars in tomato trichomes." Proceedings of the National Academy of Sciences 109.40 (2012): 16377-16382. (Year: 2012).*
The Tomato Genome Consortium. The tomato genome sequence provides insights into fleshy fruit evolution. Nature 485, 635-641 (2012). https://doi.org/10.1038/nature11119 (Year: 2012).*
Huang, Ying, et al. "AP2/ERF transcription factors involved in response to tomato yellow leaf curly virus in tomato." The Plant Genome 9.2 (2016): plantgenomeSep. 2015. Submitted via IDS of Sep. 25, 2025 (Year: 2016).*
Bolger et al., "The genome of the stress-tolerant wild tomato species *Solanum pennellii*", Nature Genetics, (2014) (46):1034-1038.
Genbank, "Solanum lycopersicum cjromosome ch01, complete genome" HG975513.1 (2015).
International Preliminary Report on Patentability for International Application No. PCT/EP21/57590 dated Sep. 12, 2023.
International Search Report and Written Opinion for International Application No. PCT/EP21/57590 dated Dec. 10, 2021.
Lawson et al., "Marker-assisted transfer of acylsugar-mediated pest resistance from the wild tomato, *Lycopersicon pennellii*, to the cultivated tomato, *Lycopersicon esculentum*", Molecular Breeding, (1997) (3):307-317.
Leckie et.al, "Quantitative trait loci regulating sugar moiety of acylsugars in tomato." Molecular Breeding (2013) (31):957-970.
Schilmiller et al., "Identification of BAHD acetytransferase that produces protective acyl sugars in tomato trichomes", Proceedings of the National Academy of Sciences, (2012) (109)40:16377-16382.
Huang et al., "AP2/ERF Transcription Factors Involved in Response to Tomato Yellow Leaf Curly Virus in Tomato." The Plant Genome, 2016, 9(2), pp. 1-15.

* cited by examiner

*Primary Examiner* — Weihua Fan
(74) *Attorney, Agent, or Firm* — Foley Hoag LLP; Brendan T. Jones

(57) ABSTRACT

The present invention relates to a tomato plant having improved insect resistance, more specifically whitefly or mite resistance, wherein the plant comprises a SlAT2 gene encoding for an acetyl-CoA-dependent acyltransferase enzyme and an AP2e gene encoding for a APETALA2 ethylene-responsive transcription factor. The present invention further relates to methods for providing a tomato plant having improved insect resistance and the use of a SlAT2 gene in combination with an AP2e gene for providing insect resistant tomato plants.

17 Claims, 9 Drawing Sheets

Figure 1:

Specification includes a Sequence Listing.

$C_{29}H_{48}O_{15}$

% dead wt compound ug/grw

> gDNA SIAT2 (SEQ ID No. 1)

```
TCACTTGTAGGGGTGGAAAAATAGACTAAACCTATATATATATTATATTATATGGTTATAAGTTTGATTAAT
CCATTTTAAAATGGTTTTGTCGTTCGAATAAAAATGAATAAAATATAAATTAATTCTGGTTACATTCGTCAA
ATATAAATATATATATTTTTTAATTAAGATATTATTTTTAATAAACACTTAAAAATTCTTCAAAATAATTGGAT
TGATTATTACCCAATTTATTATTTAGCGAAGATATTGTATAATAAGAAAAGACTTACTTTCAGAGTAACTTTC
TTTTATCTCCAAAGGAAAAGGCTTGGTTGAAGGCAAAATTTGATGTAATTTTGGAATTCCGGCATGCAAAG
TTACAAGAGTTTCACACAATAATGCTAATTATTGTAGGAATGGCTTTATCCCAAGACAAAATGAGTCCAAAT
GAGTTTTCACTTTCCCAATCAAGGACATTCTAGTTCGACATGCTACTTTCACATTCTCAATTTATTTTTAAATA
TTTGATAGATGAGTGAAACTTAATTTTCGATTTTTAGTTAGTGAGTAAATTTTCTCTCAGAATAGTTTTGGTT
ATGAGGAGAAATAAATTTATAAACTCTATTGAAAATATTGTTTGGAATTTTAGGTTTCTAGTTTATAAAGTA
TTTCCCATGTTTGGTGCCAAAATCAAGAACAACCTTTTGCCAAGAAAATGCAACAGGTAATATATAGCGAC
ATTTGACTGATATGATTTAAAATATTTACCCTGAAAATTTTGTAATTGTAAAAACTTTTAGCGTAATTAACCG
CCCAAATAAATTCTGTAGTATATACACTAGTGTTTGTTCTGAACAATGCACTTTATGAATGTTAAATGCAAT
ATATTAAAGATTGACGCCATGCCAAACTATATATATAATAGGAATGAACATTGATAGATTTATTCAGAAAC
AACACTTTATTCATCCAAAAAAAAAGATGAATTGTTATATTGAAATTCAATCAAGGAAAATGGTGAAACCC
TCAGCTCCTACCCCGGATAATCTTCGGAGATTGAAGCTTTCCTTGTTCGATCAGATGGATATTGGTGCATAT
GTACCAATTGTCTTCAACTACTTGCCGAACAGCACTTCATCATATGATCATGATGATAAGCTTGAAAAATCA
TTGTCGGAGACGCTAACCAAGTTTTACCCTTTTGCTGGAAGATTTAGAAAAGGCATTGATCCATTTTCCATC
GACTGCAATGATGAAGGTATTGAATATGTTCGAACCAAAGTCAATGCAGACGATCTTGCCCAATATCTCCG
TGGTCAAGCCCATAATGATATTGAGTCGTCTTTGATTGATCTTCTTCCTGTAATGCATCGTCTACCATCAAGT
CCATTATTTGGTGTTCAAGTGAATGTATTCAATAACGGAGGTGTAACCATAGGGATACAAATTTTACATAT
GGTATCTGATGCTTTCACTTTAGTAAAATTTGTAAATGAATGGGCGCACACCACCCTTACAGGGACGATGC
CACTAGATAATCCCGGTTTTGGTCAATTGCCATGGCTATTTCCAGCAAGAGCGCTACCGTTTCCATTACCTG
ATTTCAACACTACTACTGCCCCTAATTATAAGAATGTTACAAAGAGGTTTCTCTTTGATGCTTTGGCAATAG
AAAACCTCAGAAATACAATCAAAGCCAATGACATGATGATGAAGCAACCTTCTAGAGTGGTGGTCGTGAT
GTCCCTAATATGGAAGGTTCTTACACACATTTCTTCCGCCAAAAATAATGGAAATTCAAGGGACTCATCTTT
AGTGTTTGTTGTTAATTTGAGGGGAAAACTGTCATGTACTGCACCGTCTTTAGAACACGTTGTAGGGAATT
GTGTAATACCAGCAACTGCTAACAAGGAGGGCGATGAGGCAAGAAGAAAGGATGATGAGTTGAATGATT
TCGTTAAGTTGGTAAGAAATACAATACGGGACACATGTGAAGCCATTGGTAAGGCGGAAAGCGTTGATGA
TATTTCCTCTTTAGCATTTAACAATCTGACGAAATGTATAGAAAAAATTCTGCATGGAGACGAGATGGACTT
CTATTCGTGCTCTAGTTGGTGCGGATTCCCTTGGTATGAAGCTGACTTTGGTTGGGGAAAGCCATTCTGGG
TGAGCTCAGTTAGTTTTGGTCATCATGGAGTAACTAATCTCATGGACACAAAGATGGTGATGGAATACAA
GTAACAATTTGTTTGAAGGAGAATGACATGATTGAGTTTGAGAGAGACCCTCACATTTTGTCCTCCACTTCA
AAACTAGCATTCCATTCCTTAGGATAA
```

> cDNA SIAT2 (SEQ ID No. 2)

```
ATGAATTGTTATATTGAAATTCAATCAAGGAAAATGGTGAAACCCTCAGCTCCTACCCCGGATAATCTTCGG
AGATTGAAGCTTTCCTTGTTCGATCAGATGGATATTGGTGCATATGTACCAATTGTCTTCAACTACTTGCCG
AACAGCACTTCATCATATGATCATGATGATAAGCTTGAAAAATCATTGTCGGAGACGCTAACCAAGTTTTAC
CCTTTTGCTGGAAGATTTAGAAAAGGCATTGATCCATTTTCCATCGACTGCAATGATGAAGGTATTGAATAT
GTTCGAACCAAAGTCAATGCAGACGATCTTGCCCAATATCTCCGTGGTCAAGCCCATAATGATATTGAGTC
GTCTTTGATTGATCTTCTTCCTGTAATGCATCGTCTACCATCAAGTCCATTATTTGGTGTTCAAGTGAATGTA
TTCAATAACGGAGGTGTAACCATAGGGATACAAATTTTACATATGGTATCTGATGCTTTCACTTTAGTAAAA
TTTGTAAATGAATGGGCGCACACCACCCTTACAGGGACGATGCCACTAGATAATCCCGGTTTTGGTCAATT
```

FIG. 4

```
GCCATGGCTATTTCCAGCAAGAGCGCTACCGTTTCCATTACCTGATTTCAACACTACTACTGCCCCTAATTAT
AAGAATGTTACAAAGAGGTTTCTCTTTGATGCTTTGGCAATAGAAAACCTCAGAAATACAATCAAAGCCAA
TGACATGATGATGAAGCAACCTTCTAGAGTGGTGGTCGTGATGTCCCTAATATGGAAGGTTCTTACACACA
TTTCTTCCGCCAAAAATAATGGAAATTCAAGGGACTCATCTTTAGTGTTTGTTGTTAATTTGAGGGGAAAAC
TGTCATGTACTGCACCGTCTTTAGAACACGTTGTAGGGAATTGTGTAATACCAGCAACTGCTAACAAGGAG
GGCGATGAGGCAAGAAGAAAGGATGATGAGTTGAATGATTTCGTTAAGTTGGTAAGAAATACAATACGG
GACACATGTGAAGCCATTGGTAAGGCGGAAAGCGTTGATGATATTTCCTCTTTAGCATTTAACAATCTGAC
GAAATGTATAGAAAAAATTCTGCATGGAGACGAGATGGACTTCTATTCGTGCTCTAGTTGGTGCGGATTCC
CTTGGTATGAAGCTGACTTTGGTTGGGGAAAGCCATTCTGGGTGAGCTCAGTTAGTTTTGGTCATCATGGA
GTAACTAATCTCATGGACACAAAAGATGGTGATGGAATACAAGTAACAATTTGTTTGAAGGAGAATGACA
TGATTGAGTTTGAGAGAGACCCTCACATTTTGTCCTCCACTTCAAAACTAGCATTCCATTCCTTAGGATAA
```

> protein SIAT2 (SEQ ID No. 3)

```
MNCYIEIQSRKMVKPSAPTPDNLRRLKLSLFDQMDIGAYVPIVFNYLPNSTSSYDHDDKLEKSLSETLTKFYPFAG
RFRKGIDPFSIDCNDEGIEYVRTKVNADDLAQYLRGQAHNDIESSLIDLLPVMHRLPSSPLFGVQVNVFNNGGV
TIGIQILHMVSDAFTLVKFVNEWAHTTLTGTMPLDNPGFGQLPWLFPARALPFPLPDFNTTTAPNYKNVTKRFL
FDALAIENLRNTIKANDMMMKQPSRVVVVMSLIWKVLTHISSAKNNGNSRDSSLVFVVNLRGKLSCTAPSLEH
VVGNCVIPATANKEGDEARRKDDELNDFVKLVRNTIRDTCEAIGKAESVDDISSLAFNNLTKCIEKILHGDEMDF
YSCSSWCGFPWYEADFGWGKPFWVSSVSFGHHGVTNLMDTKDGDGIQVTICLKENDMIEFERDPHILSSTSKL
AFHSLG
```

> gDNA AP2e (SEQ ID No. 4)

```
AATGAAAAAACAAAAGGGAAATGTCATAGATTTTCTATACGAATAATTGCTATTACTTGTAATTAGAAGTG
ACATTGCGGGAGTAAGCTAAATAAAATATGTATATAACTATATAAATTTTGTACAAAATAGGACCGAATTTT
AGTCCAAAACTGTAAATGAAGAGTGTTTTTATAAATTATAAATGTTTGGATAATTTAAAATTTTAAAAAATC
CCCGAATACTTTTTCCCCCCTAATATTTGAAAACTTAGGATGGTTACCAAATATGTTTATAAAGAAATAACA
ACTTATATTTGAAAATACTTGTGGCCAAATGAAAATGAGAAACTCGTTTTTTTTAAAATTTCTATATGTAAAAT
TTAAAAATGTAATTTTTTACCAAAATATTTTCATCGTCCATAATGCACCCGCAGTCTTTTGTAAAATAAGGTC
CACTTGAAACGAAAAGCTCACGGCCCATGCAAACCTCCTGCATCATACATTAGTTAATTAGTATACTTAATT
TCAAACTTATTTATCTTAGTTTACTTTGAGTTTTTAAATTTTTGATTTTTTATATACAAAATTATGATGTTAAATTT
AAAATATATCAAATACTTTCCTATTCTGTTTTATAATGTCTACAATGAGATCTTTAATAAAAAAAGAAATTTT
ATTTTTTTGGTCCATATCAAATTATGATTTTTTTGAAACCATTATGCTAAGTTAAACTACAATTTAACTGATA
ACTAATCAATCCTCAAGGGAACTATTCATTCGGACCCATCTAGGAATCCATTATTCGTTAGCCATTTACAAG
AATAGAGACCCCATTAAGAATAATACATAAAATTAATAGTTATAATGGAGCACCCAATACTTCTTAATTTGC
ATAAAAGGTGCTTGCTTGATTTTCAATTTCCTAAAAGAGATATATATAATGTAGGTGAAGAAAATAATCTTT
CCTAATTGCCAGCGTGGATTCAAATGAGTAATTAAAAATTAAATAAATAAACATAAATATAGATTATACAA
CAAAATGAAAAGGGGGGCCCCACGTTCTGTTTTTGGTAAAAGAAATAAGAGTAATTTTTTTGTAAATTTTTC
CATATAAAACCATAGTGTTTCCCAAAATAAGAGGAACCAAAAGTAGCTTCACAAATCACACAACCCACATA
AGTTGCCTCACACGTCCCATCTTTCTTCTTCCCCAACCCCTACCCCCTATCTACTGCTCCTATGGAGTACTATA
ACTAAATGAAATTCATCTCAATTTATTCTTCTTCCATTGACGCTTACAATCATTTTGGTTAACTCCCACAGATA
TTTTATAGTTAGTCAAAAACAGAACAATGTTGGATCTCAATGTAAGCGTAATCTACAGTAATGACCTTCCAC
AAGTTTCTCTACTTGATGAATCAGCCACCTCCAATTCATCCTTACGAAATGCGGAAGCTACAACCAGTGCCG
GTGACGAAGATTCGTGCGCCGGTGAGTTGTTCGCTTTCAATTTTGGAATCCTCAAAGTTGAAGGAGCTGAG
ACTAGTAGGAGCAGCAACAACGATGATGAGGAAGCATACGGTAAGAATCAGAGAGTTACTCATTCTCAAT
TCGTGACTAGGCAGCTGTTTCCCGTTGATGATGGTGAGTTGAACCGGAAACAAACCGATCGGGTCATTCTC
TCCTCCGCTCGATCCGGTACTTCTATCGGTTTTGGAGATGTGCGGATAATACAACAGCAACAAACGGAGCA
ACCGAAACAACAAGTGAAGAAGAGTAGGAGAGGCCCAAGGTCAAGAAGTTCACAGTACGAGGTGTCAC
```

<p style="text-align:center"><strong>FIG. 4 (Cont.)</strong></p>

```
TTTCTACCGTAGAACTGGTAGATGGGAATCACATATATGGTTAGTTTTCTAACTGATTTTTTTTTTGTTGATA
GGATGATGATTAATTGGCAAATGATAAATTGTCAATTTTATTAATATAACTACAATTGGATGCAGGGACTG
TGGGAAACAAGTATATTTGGGTATGGATATTGCTATTTTAAATATACAGTTTGGTTAATTTCGTTGTTTTTGT
GGATTTTGGTGCTAAAGCTGTGTCTATACTTTTTGCTAATTTTTGATTGTTTTTTTTTGTTGCTTTATATTAGG
TGGTTTTGATACTGCTCACACAGCAGCAAGGTAAAATAAAAGTCATATGAGTTCTCAAATATACGCGTCAT
CAGATTTTTCAAATTTATGCTATTTCCCAAATTTGATTGTATTTGTTTCTTCTCCGTTGTACAGAGCTTATGA
CAGAGCTGCAATTAAATTTAGGGGTGTTGATGCTGATATCAACTTTAGCTTAAGTGATTACGAGGAGGATA
TGCAACAGGTTAGAAATGCAAAGATTTAATATGTGCAAATATGTTAAAGTCACTGTTGAGCGCTTCTCTGG
GTTTATTATTGCTTCTGTTTTAATTGGCATCAATAATATGAATCATATACAAGTATTCTGAACTATTTGGTGG
ACACCTTTTTTTGATTTACGCAGATGAAAAACCTTGGTAAAGAAGAATTTGTGCACTTGCTGCGACGCCATA
GCACTGGTTTCTCAAGAGGGAGCTCCAAATTCAGAGGAGTGACGCTACATAAATGTGGCAGATGGGAGGC
TCGGATGGGACAGTTCCTCGGGAAAAAGTAAGGAACTCACTCACTCATTGAAATTCTCGAAGAAGTAGATT
ACATCTTATTATAGTAATTGGTCAAAAATGGGACATACATATGTTTAAATTGCGTATTTGAAGAAGAAATCA
TTGGGACAACAGTATTCATAGTGGGGATTGCACTGCTTATATTGCAGGTATATATATCTTGGGCTGTTCGA
CAGCGAAGTAGAAGCTGCAAGGTCCTAATGATAATGAATTACCCTCTCTCTGATGATGAACATTTATCCTAA
ATTTTCAACTTTAATTATGTGTCATCTAACCGGTATCTCCTTTATTTTTTTGCAAATCAGGGCCTACGATAAG
GCGGCAATTAAAACTAGCGGAAGGGAAGCTGTTACCAACTTTGAGCCAAGTAGCTATGAAGGGGAAACA
ATGTCTTTACCACAGAGTGAAGGTTTGCTCAAAAGTTCTTGGTCATTTCCAAACTAATATAGATACATGCAA
CAGTAGTATCTATATGTGGATCTATCTCATTTGTGATGCCTATGATGCAGGTAGCCAACATGATCTTGATCT
GAACTTGGGGATATCGACCACTTCTTCAAAGGAAAATGACAGGTTGGGAGGTTCTCGCTATCATCCTTACG
ATATGCAAGACGCAACAAAACCTAAGGTATTAGCAGAGTAGCTTATATGCTTCTGTTCTTGCAAAATCAATT
GGATTAAAATGCTCTCCTTTATGTTATAGTCTTCTATTGTTACTTCTTTCATAGATAATATGCAAGAGATCTA
TTGCAGTAATTCATGAGTATTAGTTATTGGTAGTAATATAATCTCCTTTTTGTTAATTTAGATAGCTTTTCCC
ATTCATACATAATTGTGATAAAACATGTTCATGAGCATTGTTAATCTTTCGTTTTTGTAGATTGTAATAATCT
ATTTGTGCTCTTTAACTATAGATGGATAAACCTGGTTCAGTAATAGTTGGAAGTTCACATCTCAAGGGACTA
TCAATGTCGTCCCAACAAGCTCAATTGTGGACTGGAATCTATTCTAATTTCTCTTCCAGCTATGAGGTAAAA
TACTAACTCTACCATCAGTCAGAAATTTGGGACCAAATACAGTGATGAAACTCCAATTTATCTCTGTTTAGT
CTTCTTTTCCTCACTTATCGTCAAATTAGCACGTATTCAGTTGCCAAAATAGCCATATTCATGCCCCCTTACCC
CAATTTCCCTCAAGTGCTGGGACCATTTGTGTTGTATGAAATGTTTTACCTTTTTCCTTCTAGTTCTTTGCATT
GTCTTCAGTTGCCAAAATAACTATCTCCATCCCCGAAGCCCAATTTCTCTGAAGTACTGAAATTATTTGTCTT
GTATGAAACATTTTACCTTTTTACTTCTTGTGTTTTTTGGGGCTGATAATCAGTGATAGTATGCCCCATGACA
AATGATAATATTGTTGTGGGATCGTACACCCCATGATAAGATTTATCTTTAACTTAACAAAATTTCTTTGTAC
TTAGTCAATCATTTGGATAATCATGAGCTATGTTATACTTGGGGTGCATATTCTCATGTGTGGTCACAGCCA
GTTTTTCACTGCAAACAGTTGTCTAAAAGTCAATGTCTTTGTTATGCCCTTTTGTGCCTCTTCTTAATTGAAT
GCATCCTTAGTGTAACCTTCCAAAACCCTCTCTCTGTTAATTTAACTAATAATCATATGGCAGGGAAGAGCA
TATGACAAGAGAAAGGACACAGGTTCATCACAAGGACCTCCAAATTGGGCATTGCAAATGCCTAGTCAGG
TTGATACAAACAGCCCATTGACAATGTTCTGCACGGCATCATCATCAGGATTCTTCATTCCATCTACTACTTC
TGTCACTTCATCAACATCTGCATTAGCAACTTCAACAAATGCCTCGCAGTGCTTTTACCAGATTAATCCCCGC
CTACCACTTCCATAA
> cDNA AP2e (SEQ ID No. 5)
ATGTTGGATCTCAATGTAAGCGTAATCTACAGTAATGACCTTCCACAAGTTTCTCTACTTGATGAATCAGCC
ACCTCCAATTCATCCTTACGAAATGCGGAAGCTACAACCAGTGCCGGTGACGAAGATTCGTGCGCCGGTGA
GTTGTTCGCTTTCAATTTTGGAATCCTCAAAGTTGAAGGAGCTGAGACTAGTAGGAGCAGCAACAACGATG
ATGAGGAAGCATACGGTAAGAATCAGAGAGTTACTCATTCTCAATTCGTGACTAGGCAGCTGTTTCCCGTT
GATGATGGTGAGTTGAACCGGAAACAAACCGATCGGGTCATTCTCTCCTCCGCTCGATCCGGTACTTCTAT
```

FIG. 4 (Cont.)

CGGTTTTGGAGATGTGCGGATAATACAACAGCAACAAACGGAGCAACCGAAACAACAAGTGAAGAAGAG

TAGGAGAGGCCCAAGGTCAAGAAGTTCACAGTACAGAGGTGTCACTTTCTACCGTAGAACTGGTAGATGG

GAATCACATATATGGGACTGTGGGAAACAAGTATATTTGGGTGGTTTTGATACTGCTCACACAGCAGCAAG

AGCTTATGACAGAGCTGCAATTAAATTTAGGGGTGTTGATGCTGATATCAACTTTAGCTTAAGTGATTACG

AGGAGGATATGCAACAGATGAAAAACCTTGGTAAAGAAGAATTTGTGCACTTGCTGCGACGCCATAGCAC

TGGTTTCTCAAGAGGGAGCTCCAAATTCAGAGGAGTGACGCTACATAAATGTGGCAGATGGGAGGCTCG

GATGGGACAGTTCCTCGGGAAAAAGTATATATATCTTGGGCTGTTCGACAGCGAAGTAGAAGCTGCAAGG

GCCTACGATAAGGCGGCAATTAAAACTAGCGGAAGGGAAGCTGTTACCAACTTTGAGCCAAGTAGCTATG

AAGGGGAAACAATGTCTTTACCACAGAGTGAAGGTAGCCAACATGATCTTGATCTGAACTTGGGGATATC

GACCACTTCTTCAAAGGAAAATGACAGGTTGGGAGGTTCTCGCTATCATCCTTACGATATGCAAGACGCAA

CAAAACCTAAGATGGATAAACCTGGTTCAGTAATAGTTGGAAGTTCACATCTCAAGGGACTATCAATGTCG

TCCCAACAAGCTCAATTGTGGACTGGAATCTATTCTAATTTCTCTTCCAGCTATGAGGGAAGAGCATATGAC

AAGAGAAAGGACACAGGTTCATCACAAGGACCTCCAAATTGGGCATTGCAAATGCCTAGTCAGGTTGATA

CAAACAGCCCATTGACAATGTTCTGCACGGCATCATCATCAGGATTCTTCATTCCATCTACTACTTCTGTCAC

TTCATCAACATCTGCATTAGCAACTTCAACAAATGCCTCGCAGTGCTTTTACCAGATTAATCCCCGCCTACCA

CTTCCATAA

> protein AP2e (SEQ ID No. 6)

MLDLNVSVIYSNDLPQVSLLDESATSNSSLRNAEATTSAGDEDSCAGELFAFNFGILKVEGAETSRSSNNDDEEA

YGKNQRVTHSQFVTRQLFPVDDGELNRKQTDRVILSSARSGTSIGFGDVRIIQQQQTEQPKQQVKKSRRGPRS

RSSQYRGVTFYRRTGRWESHIWDCGKQVYLGGFDTAHTAARAYDRAAIKFRGVDADINFSLSDYEEDMQQM

KNLGKEEFVHLLRRHSTGFSRGSSKFRGVTLHKCGRWEARMGQFLGKKYIYLGLFDSEVEAARAYDKAAIKTSG

REAVTNFEPSSYEGETMSLPQSEGSQHDLDLNLGISTTSSKENDRLGGSRYHPYDMQDATKPKMDKPGSVIVG

SSHLKGLSMSSQQAQLWTGIYSNFSSSYEGRAYDKRKDTGSSQGPPNWALQMPSQVDTNSPLTMFCTASSSG

FFIPSTTSVTSSTSALATSTNASQCFYQINPRLPLP

FIG. 4 (Cont.)

TOMATO PLANT HAVING IMPROVED INSECT RESISTANCE

RELATED APPLICATIONS

This application is a U.S. National Phase of International Patent Application No. PCT/EP2021/057590, filed Mar. 24, 2021, which is hereby incorporated by reference in its entirety.

The present invention relates to a tomato plant having improved insect resistance, more specifically whitefly or mite resistance, wherein the plant comprises a SlAT2 gene encoding for an acetyl-CoA-dependent acyltransferase enzyme and an AP2e gene encoding for a APETALA2 ethylene-responsive transcription factor. The present invention further relates to methods for providing a tomato plant having improved insect resistance and the use of a SlAT2 gene in combination with an AP2e gene for providing insect resistant tomato plants.

Whiteflies are of the family Aleyrodidae that typically feed on the abaxial side of plant leaves. There are more than 1500 species been described and especially in warm or tropical climates and in greenhouses, whiteflies present a major problem in crop protection in warm climates and crops grown under greenhouse conditions, resulting in huge economic losses annually worldwide. Many whitefly species are very small in size which complicates their control in greenhouses, and when leaving unchecked whitefly populations in greenhouses rapidly become overwhelming. Whitefly related damage reduces crop quality and quantity, such as a reduction of plant vigour and yield, early wilting, leaf chlorosis and defoliation. The silverleaf whitefly (*Bemisia tabaci*) is one species of whitefly that are currently one of the most important agricultural pests.

Although several species of whitefly may cause some crop losses simply by sucking sap when they are very numerous, the major harm they do is indirect. The major importance as crop pests is their role as vectors and in the transmission of diseases of plants, including more than 200 plant viruses. Furthermore, whiteflies feed by tapping into the phloem of plants, introducing toxic saliva and decreasing the plants' overall turgor pressure. The whitefly secrete large amounts of honeydew that support harmful infestations of fungi like sooty mold. Since whiteflies congregate in large numbers, susceptible plants can be quickly overwhelmed.

Insecticides such as neonicotinoid, organochlorines, and organophosphate compounds are widely used and are an effective way to control whiteflies. However, continuous application of insecticides results in the development of whiteflies becoming resistant. In addition more environmental friendly, biological methods have also been proposed to control whitefly infestation, such as using natural predators and parasitoids (e.g. using green lacewing larvae) to control whitefly infestations, or washing of the plants to reduce the number of the pests on the plants. However, also these methods do not provide an optimal solution to the pests, and whitefly remains difficult to control.

Especially in tomato (*Solanum lycopersicum*) and pepper (*Capsicum* spp.) whitefly infestations prove to be a problem. Tomato is classified as *Solanum* sect. *Lycopersicon* comprising 13 species, of which *Solanum lycopersicum* is the cultivated tomato, whereas the other 12 species are wild relatives. The genus *Capsicum* has 25 species of which five are cultivated, including *C. annuum, C. chinense, C. baccatum, C. pubescens* and *C. frutescens*. The domestication of tomato and pepper resulted in loss of genetic diversity which makes them prone to abiotic and biotic stresses such as pest attacks. To date, no cultivated tomato and sweet peppers are resistant to whiteflies. Previously several studies have been performed to find whitefly resistance in wild relatives of tomato and sweet pepper. Several wild relatives of tomato (*S. pennellii, S. habrochaites, S. peruvianum* and *S. pimpinellifolium*) are known to be more resistant than the cultivated material.

Antibiosis is one of the resistance mechanisms in which a plant exerts an adverse influence on the growth and survival of the insect. One of the most prominent tomato characters that contribute to whitefly antibiosis are trichomes, which are fine outgrowths or appendages on plants, such as glandular hairs. Their function is to secrete metabolites for the plant, including terpenoids, phenylpropanoids, flavonoids, methyl ketones and acyl sugars having diverse functions in the plant related to growth and development, and stress response. For example, mono- and sesquiterpenes, methyl ketones and acyl sugars are secondary metabolites that are known to be associated with whitefly resistance in tomato. Although glandular trichomes seem to play an important role in whitefly resistance, it is actually the compounds within the trichomes that are decisive. A high correlation was found between presence of specific trichomes (type IV trichomes) and whitefly resistance and previous studies showed that whitefly resistance is based on several mechanisms involving many genes and is a complex process. Efforts of introducing whitefly resistance in the cultivated tomato were not successful and new approaches and resistant sources should be considered.

Considering the above, there is a need in the art for tomato plants having an improved insect resistance, more specifically tomato plants having improved insect resistance. In addition, there is a need in the art for a method for providing plants having improved insect resistance, more specifically tomato plants having improved resistance against whiteflies.

It is an object of the present invention, amongst other objects, to address the above need in the art. The object of present invention, amongst other objects, is met by the present invention as outlined in the appended claims.

Specifically, the above object, amongst other objects, is met, according to a first aspect, by the present invention by a tomato plant having improved whitefly resistance, wherein said plant comprises a combination of an acetyl-CoA-dependent acyltransferase gene (SlAT2) encoding a cDNA sequence having at least 95%, preferably at least 98%, more preferably at least 99% sequence identity with SEQ ID No. 2, and an APETALA2e ethylene-responsive transcription factor gene (AP2e) encoding a cDNA sequence having at least 95%, preferably at least 98%, more preferably at least 99% sequence identity with SEQ ID No. 5, wherein said combination of SlAT2 and AP2e genes result in an increased $C_{29}H_{48}O_{15}$ and $C_{36}H_{62}O_{15}$ acyl sugar content as compared to a tomato plant not comprising said combination of genes. Even more preferably the SlAT2 gene encodes a cDNA of SEQ ID No. 2 and the AP2e gene encodes a cDNA of SEQ ID. No. 5.

The tomato plant of present invention, preferably a *S. lycopersicum* plant has improved insect resistance, wherein the plant comprises a SlAT2 gene in combination with and an AP2e gene. The APETALA2 (AP2) gene family (sometimes also called the AP2/ethylene-responsive element-binding factor (ERF) gene family or ERF/AP2 gene family) defines a large gene family (>100+ genes) of DNA-binding proteins called AP2/ERF in tomato plants. The AP2 genes perform an array of functions including hormone regulation, the establishment of the floral meristem organ identity, and regulation and growth of floral organs and development, as well as various responses to environmental stimuli and stress responses. Furthermore, it is known that various different AP2 genes provide for changes in the ratio of hexose to sucrose during seed development of a plant, and that the AP2 protein regulates the amount of sugars in the system and is involved in transportation, shaping, and signalling in said plant using these various sugars. Surprisingly it was found that the SlAT2 gene in combination with the AP2e gene promotes and regulates the production of the type of specific acyl sugars $C_{29}H_{48}O_{15}$ (S4:C17 acyl sucrose) and/or $C_{36}H_{62}O_{15}$ (S4:C24 acyl sucrose), and that these specific increased production of acyl sugars are linked with high levels of insect resistance in the plant. The SlAT2 gene encodes for an acetyl-CoA-dependent acyltransferase enzyme and AP2e genes encode for APETALA2e ethylene-responsive transcription factor that is involved in the regulation of acyl sugars being produced. It seems that AP2e is related to the capacity of producing general amounts of different types of acyl sugars, while the SlAT2 promotes the production of the specific acyl sugars that impact the insect resistance in the plant. The AP2e effects the total amount of acyl sucrose produced by switching on genes involved in the biosynthetic pathway and formation of trichomes, whereas SlAT2 has a strong effect on the final type of acyl sucrose produced. An active SlAT2 enzyme is responsible for adding an additional acetyl-group to acyl sucrose that has already three acyl-groups. This results in an increase of the amount of tetra-acyl sucrose at the expense of tri-acyl sucrose, which results in an improved insect resistance as observed in tomato plants. It is an additional step to a series of reactions that are catalysed by SlAT type of enzymes different from SlAT2; different Acyl-Co transferases which only add up to three acyl chains to the initial sucrose molecule and hence only contribute indirectly to insect resistance.

According to another preferred embodiment, the present invention relates to the tomato plant, wherein said plant comprises tetra-acyl (S4) sugar and tri-acyl (S3) sugars, wherein the ratio between tetra-acyl (S4) sugars and tri-acyl (S3) sugars (S4:S3) in the plant is at least 1, preferably at least 1.2, more preferably at least 1.5, most preferably at least 1.7. Experiments show that the type of acyl sugars is crucial for providing the whitefly resistance in tomato plants. It was observed that plants comprising the AP2e gene and producing acyl sugars are not always resistant for whitefly. However in case the plant also comprise the SlAT2 gene, the plant show improved insect resistance which was shown to be linked to high levels of tetra-acyl (S4) sucroses, for example high $C_{29}H_{48}O_{15}$ (S4:C17) and $C_{36}H_{62}O_{15}$ (S4:C24), in comparison to susceptible plants that mostly accumulated tri-acyl sucroses (S3).

The tomato plant of present invention has increased $C_{29}H_{48}O_{15}$ and/or $C_{36}H_{62}O_{15}$ acyl sugar content in comparison to a plant that does not comprise the SlAT2 gene in combination with the AP2e gene. The acyl sugars are trichome exudates, more specifically the $C_{29}H_{48}O_{15}$ (S4:C17 acyl sucrose) and $C_{36}H_{62}O_{15}$ (S4:C24 acyl sucrose) acyl sugars are type IV trichrome exudates, that cause resistance to insects in tomato plants. AP2e is involved in both trichome development and acyl sugar production. Tomato plants comprising the AP2e gene have an increase of type IV trichomes in the leaf surface and stem. Many trichome exudates of tomato (approx. 90%) are comprised of acyl sugars, of which more than 70 compounds are known. The acyl sugars produced in tomato consist of different combinations of acyl groups, originating from different aliphatic acids with varying chain length and esterified to the hydroxyl groups of glucose or sucrose. The acyl chains are primarily of short to medium chain length aliphatic acids with either a branched or strait chain. In tomato it has been shown that the primary short acyl chains of acyl sugar are either acetate (C2) or branched chain amino acid derived, i.e. 2-methyl-propanoic acid (C4) and 3-methyl-butanoic acid (C5). Longer acyl groups are probably derived from beta-oxidation products of fatty acids. However, the presence and abundance of specific acyl sugars differ significantly between resistant and susceptible plants, wherein specifically $C_{29}H_{48}O_{15}$ and $C_{36}H_{62}O_{15}$ acyl sugar content is high in insect resistant plants. These acyl sugars are sticky substances that act as a glue trap and are also toxic for insects, more specifically whiteflies, providing improved insect resistance for the plant. Furthermore, not only white-flies but other pierce-sucking insects avoid settling on leaves in the presence of these specific acyl sugars.

According to a preferred embodiment, the present invention relates to the tomato plant, wherein the whitefly is one or more selected from the group consisting of *Aleurocanthus woglumi* (citrus blackfly), *Aleyrodes proletella* (cabbage whitefly), *Bemisia tabaci* (silverleaf whitefly), *Trialeurodes vaporariorum* (greenhouse whitefly), preferably *Trialeurodes vaporariorum* and/or *Bemisia tabaci*.

According to a preferred embodiment of the present invention the present plants detailed above are not plants exclusively obtained by means of an essentially biological process.

Although the present genomic regions or fragments can be introduced into tomato plants by introgression, because the nucleotide sequences of the present genomic fragments are known, these genomic fragments, for example, can be artificially constructed in yeast and subsequently allowed to recombine with susceptible tomato genomes. Alternatively, these genomic regions or fragments can be amplified by long-range PCR amplifications and the resulting amplification fragments can be transformed into spinach cells in a single step or in a series of transformations ultimately resulting in the present tomato plants. The present genomic fragments, completely or in parts later to be reassembled, can also be isolated from gels or columns for example after restriction digestion, and subsequently transformed into tomato cells. Furthermore, mutations, deletions or insertions in the genome can be obtained via EMS mutagenesis, and/or CRISPR technology. Yet alternatively, the genomic fragments of interest can be introduced into a vector under a (strong) promotor. Subsequently, susceptible plants can be transformed with the vector and the sequence of interest would be expressed resulting in resistance. These techniques are readily available for the skilled person. Construction of artificial chromosomes comprising the present genomic fragments is also contemplated within the context of the present invention.

According to another preferred embodiment, the present invention relates to the tomato plant, wherein the genomic region encoding the SlAT2 gene having at least 95%, preferably at least 98%, more preferably at least 99% sequence identity with SEQ ID No. 1 and wherein the genomic region encoding the AP2e gene having at least 95%, preferably at least 98%, more preferably at least 99% sequence identity with SEQ ID No. 4. SEQ ID No. 1 and SEQ ID No. 4 are the genomic regions comprising the SlAT2 and AP2e gene respectively including their respective promotor elements. having at least 95%, preferably at least 98%, more preferably at least 99% sequence identity with According to yet another preferred embodiment, the present invention relates to the tomato plant, wherein the SlAT2 gene encodes for the protein sequence represented by SEQ ID No. 3, and wherein the AP2e gene encodes for the protein sequence represented by SEQ ID No. 6.

According to another preferred embodiment, the present invention relates to the tomato plant, wherein the wherein the SlAT2 gene encodes for the coding sequence of SEQ ID No. 2 and the AP2e gene encodes for the coding sequence of SEQ ID No. 5.

According to yet another preferred embodiment, the present invention relates to the tomato plant, wherein the acyl sugar content of $C_{29}H_{48}O_{15}$ is at least 150 µg/g fresh weight (FW) of plant leaves, preferably at least 200 µg/g FW of plant leaves, more preferably at least 250 µg/g FW of plant leaves and/or wherein the acyl sugar content of $C_{36}H_{62}O_{15}$ is at least 125 µg/g FW of plant leaves, preferably at least 175 µg/g FW of plant leaves, more preferably at least 250 µg/g FW of plant leaves. The fresh weight (FW) is the weight of a plant or plant part, in this case plant leaves when harvested. Experiments of the bioassay show that at the claimed acyl sugar concentrations level of resistance is observed of a whitefly mortality of on average 40% or higher.

According to yet another preferred embodiment, the present invention relates to the tomato plant, wherein the plant is obtainable from deposit NCIMB 43748 at NCIMB Ltd, Ferguson Building, Craibstone Estate, Bucksburn, Aberdeen AB21 9YA, Scotland on 18 Mar. 2021.

According to another preferred embodiment, the present invention relates to the tomato plant, wherein the plant furthermore has an increased acyl sugar content of one or more selected from the group consisting of $C_{28}H_{46}O_{15}$, $C_{34}H_{58}O_{15}$ and $C_{35}H_{60}O_{15}$ in comparison to a plant that does not comprise the SlAT2 gene and AP2e gene. Next to the acyl sucrose compounds $C_{29}H_{48}O_{15}$, $C_{36}H_{62}O_{15}$, $C_{28}H_{46}O_{15}$, $C_{34}H_{58}O_{15}$, $C_{35}H_{60}O_{15}$, two additional sugars $C_{33}H_{56}O_{15}$, and $C_{37}H_{64}O_{15}$ were found to be present in higher concentrations (although less pronounced) in resistant tomato plants in comparison to their susceptible counterparts.

According to yet another preferred embodiment, the present invention relates to the tomato plant, wherein the acyl sugar content of $C_{28}H_{46}O_{15}$ is at least 10 µg/g fresh weight (FW) of plant leaves, preferably at least 15 µg/g fresh weight (FW) of plant leaves, more preferably at least 20 µg/g fresh weight (FW) of plant leaves, and/or wherein the acyl sugar content of $C_{34}H_{58}O_{15}$ is at least 15 µg/g fresh weight (FW) of plant leaves, preferably a at least 20 µg/g fresh weight (FW) of plant leaves, more preferably at least 25 µg/g fresh weight (FW) of plant leaves, and/or wherein the acyl sugar content of $C_{35}H_{60}O_{15}$ is at least 12.5 µg/g fresh weight (FW) of plant leaves, preferably at least 15 µg/g fresh weight (FW) of plant leaves, more preferably at least 20 µg/g fresh weight (FW) of plant leaves.

According to another preferred embodiment, the present invention relates to the tomato plant, wherein the plant is furthermore resistant to mite, preferably spider mite (*Tetranychus urticae*).

The present invention, according to a second aspect, relates to seeds, fruits or plant part of a tomato plant of present invention.

The present invention, according to a further aspect, relates to a method for providing a tomato plant having improved whitefly resistance, the method comprises the steps of providing an whitefly susceptible tomato plant and mutating its genome comprising;
    providing a combination of an acetyl-CoA-dependent acyltransferase gene (SlAT2) encoding a cDNA sequence having at least 95% sequence identity with SEQ ID No. 2, and an APETALA2e ethylene-responsive transcription factor gene (AP2e) encoding a cDNA sequence having at least 95% sequence identity with SEQ ID No. 5, wherein said combination of SlAT2 and AP2e genes result in an increased $C_{29}H_{48}O_{15}$ and $C_{36}H_{62}O_{15}$ acyl sugar content as compared to a tomato plant not comprising said combination of genes.

The present invention, according to a further aspect, relates to a method for providing a tomato plant having improved whitefly resistance, wherein the method comprises the steps of;
    a) crossing of a tomato plant that is susceptible to whitefly with a whitefly resistant tomato plant of present invention as defined,
    b) selecting *S. lycopersicum* plants having improved insect resistance that comprise the SlAT2 gene and AP2e gene. The selection of tomato plants having improved insect resistance can be based on the determination of $C_{29}H_{48}O_{15}$ and/or $C_{36}H_{62}O_{15}$ acyl sugar content, wherein the acyl sugar content of $C_{29}H_{48}O_{15}$ is at least 150 µg/g fresh weight (FW) of plant leaves, preferably at least 200 µg/g FW of plant leaves, more preferably at least 250 µg/g FW of plant leaves and/or wherein the acyl sugar content of $C_{36}H_{62}O_{15}$ is at least 125 µg/g FW of plant leaves, preferably at least 175 µg/g FW of plant leaves, more preferably at least 250 µg/g FW of plant leaves. Furthermore, selection of whitefly resistant tomato plants can also be done by determination or identification of the specific sequences (cDNA, gDNA or protein sequences) of SlAT2 and AP2e, as identified herein as SEQ ID NO. 1 to SEQ ID NO. 6.

According to another preferred embodiment, the present invention relates to the method, wherein the selection of *S. lycopersicum* plants having improved insect resistance is by determination of $C_{29}H_{48}O_{15}$ and/or $C_{36}H_{62}O_{15}$ acyl sugar content, wherein the acyl sugar content of $C_{29}H_{48}O_{15}$ is at least 150 µg/g of fresh weight (FW) of plant leaves and/or wherein the acyl sugar content of $C_{36}H_{62}O_{15}$ is at least 125 µg/g of fresh weight (FW) of plant leaves.

The present invention, according to a further aspect, relates to a combination of two genomic regions for providing insect resistance in tomato plants, wherein one genomic region comprising SEQ ID No. 1 that encodes an acetyl-CoA-dependent acyltransferase gene (SlAT2) and a second genomic region comprising SEQ ID No. 4 that encodes an APETALA2e ethylene-responsive transcription factor gene (AP2e).

The present invention, according to a further aspect, relates to a combination of two genes for providing insect resistance in tomato plants, wherein one gene encodes an acetyl-CoA-dependent acyltransferase (SlAT2) protein comprising SEQ ID No. 3 and a second gene that encodes an APETALA2e ethylene-responsive transcription factor (AP2e) comprising SEQ ID No. 6.

The present invention, according to a further aspect, relates to the use of a combination of the two genomic regions or two genes as defined above in tomato plants for providing whitefly resistant tomato plants.

The present invention will be further detailed in the following examples and figures wherein:
    FIG. 1: Shows the leaves of a tomato plant (*S. lycopersicum*) according to present invention (A and B) and an insect susceptible tomato plant (*S. lycopersicum*) (C and D). Both tomato plants have been exposed to a whitefly infestation in a commercial greenhouse where a whiteflies infestation was promoted. The leaves of the plants of present invention are free from whitefly infestation, whereas the leaves of the insect susceptible tomato plant are clearly infected by whitefly. Figure E shows the leaves of the insect susceptible tomato plant (S) and of the tomato plant according to present invention (R); it is clear that the whitefly are alive and on the leaf surface of the S plant, whereas on the R plant the whiteflies are dead and absent on the leave surface.

Figure 2A:
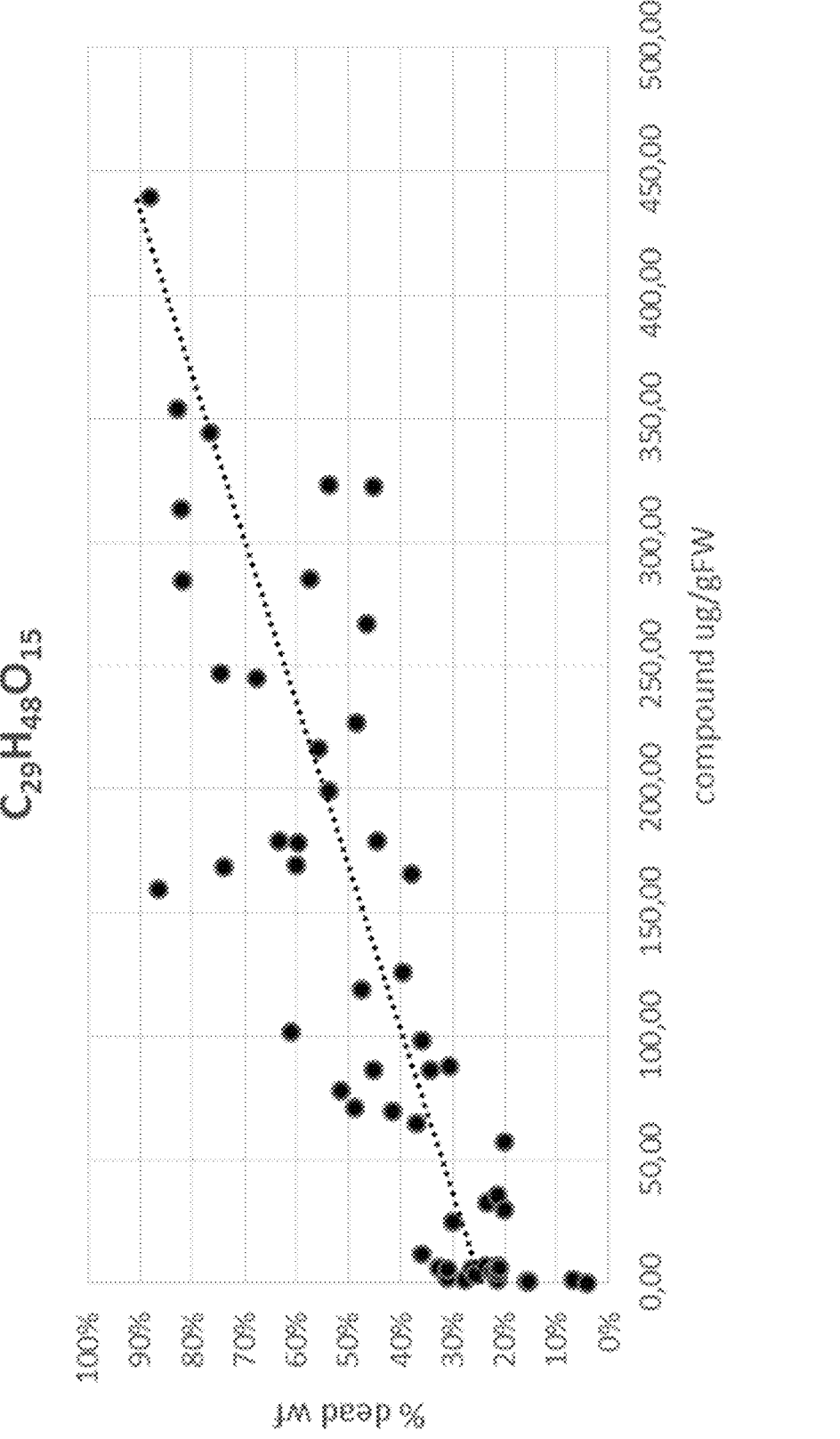
Figure 2B:
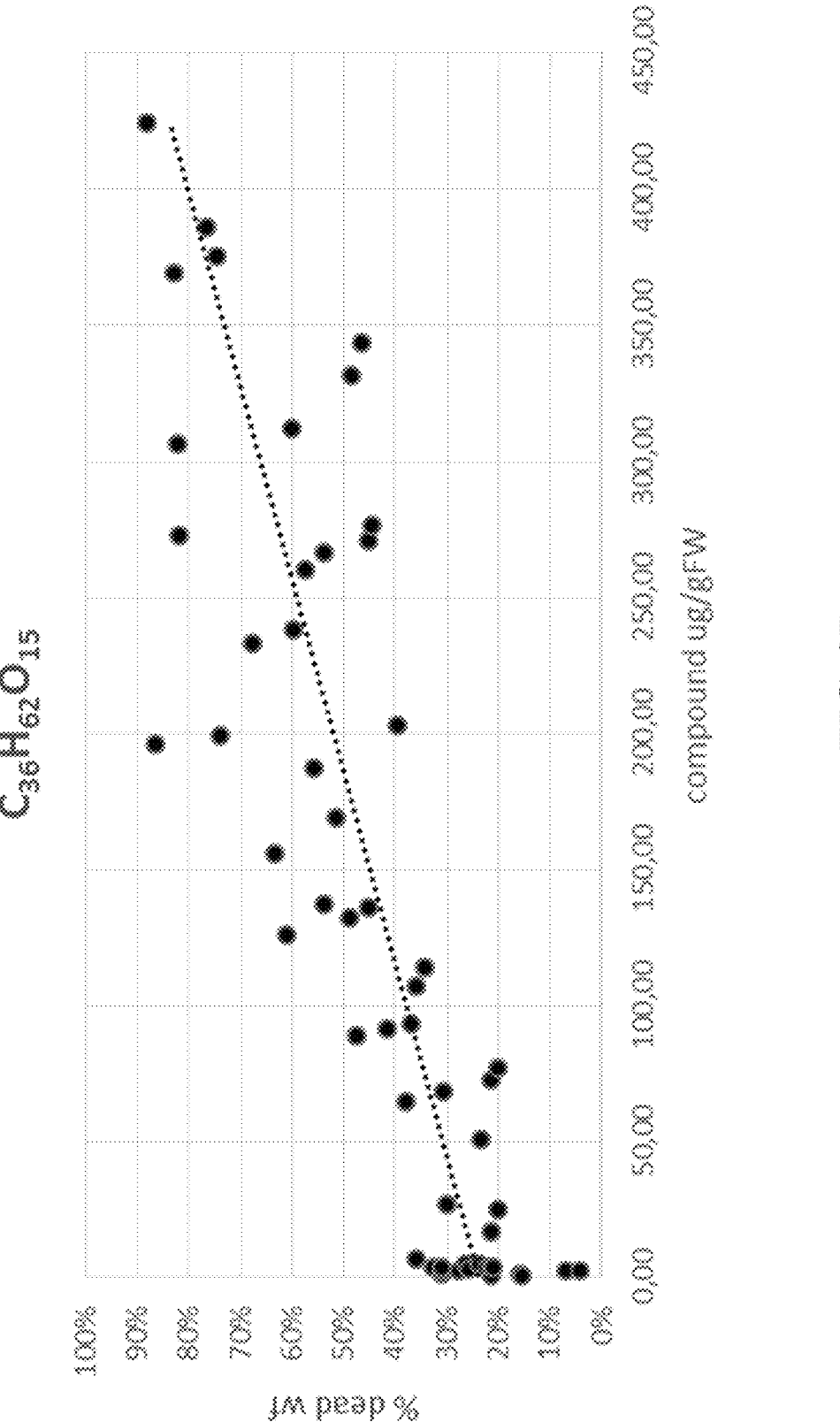
Figure 2C:
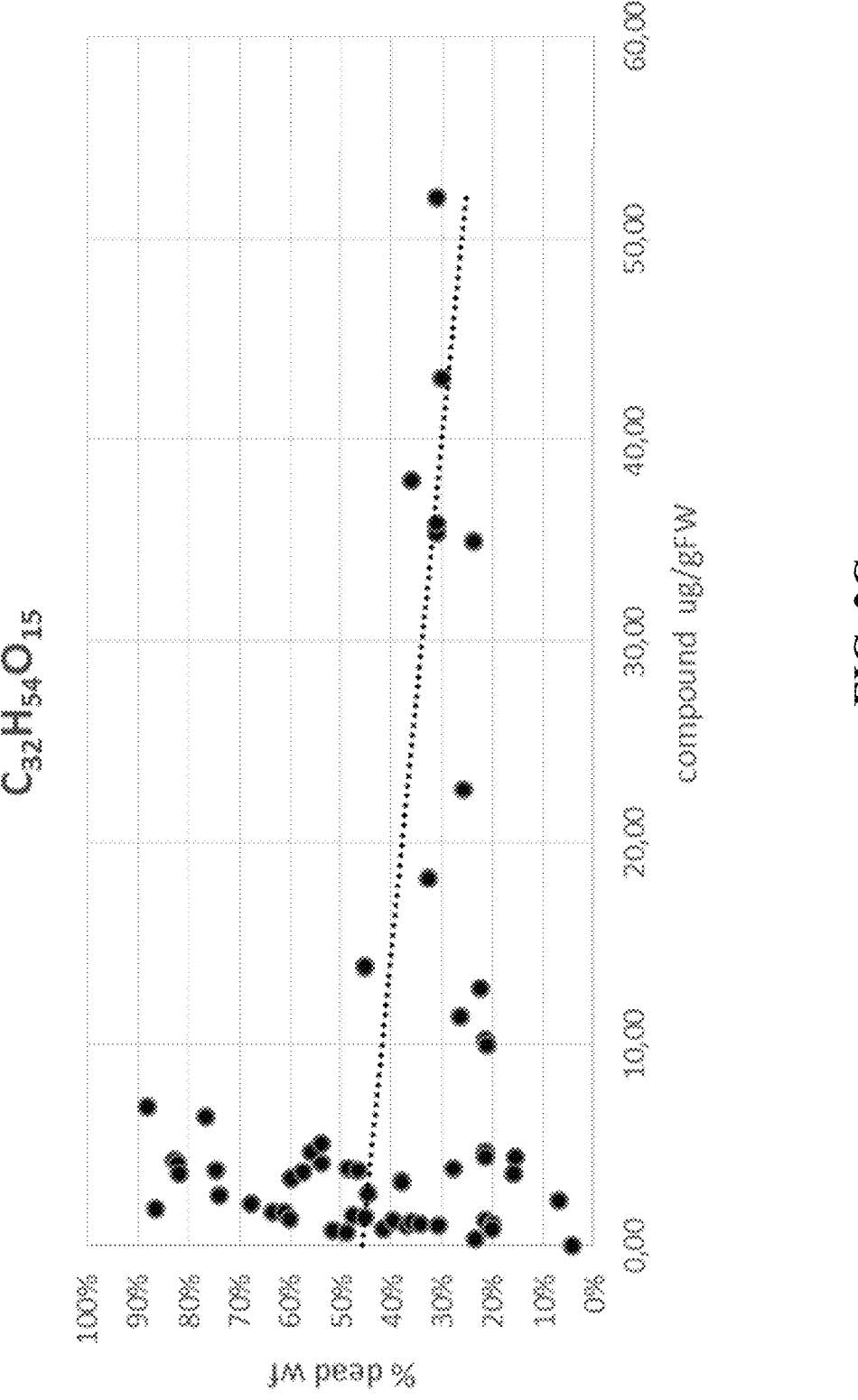

FIG. 2: Shows the ratio of dead whiteflies (WF) in against increasing concentrations of acyl sugar in a tomato plant. The graph 2A shows that there is a linear relationship between the number of dead whiteflies and the concentration of acyl sugar C36H62O15. The graph 2B shows the dose response of C29H48O15 acyl sugar. Both specific acyl sugars show to negatively affect the survival of the whiteflies. On the other hand, other acyl sugars present in the plant like C32H54O15 (graph 2C) does not affect the whiteflies as such. The fresh weight (FW) is the weight of a plant, in this case FW of plant leaves when harvested. The bioassay shows that the level of acyl sugar content in the leaves of the plant directly affects the level of resistance that is observed as whitefly mortality.

Figure 3:
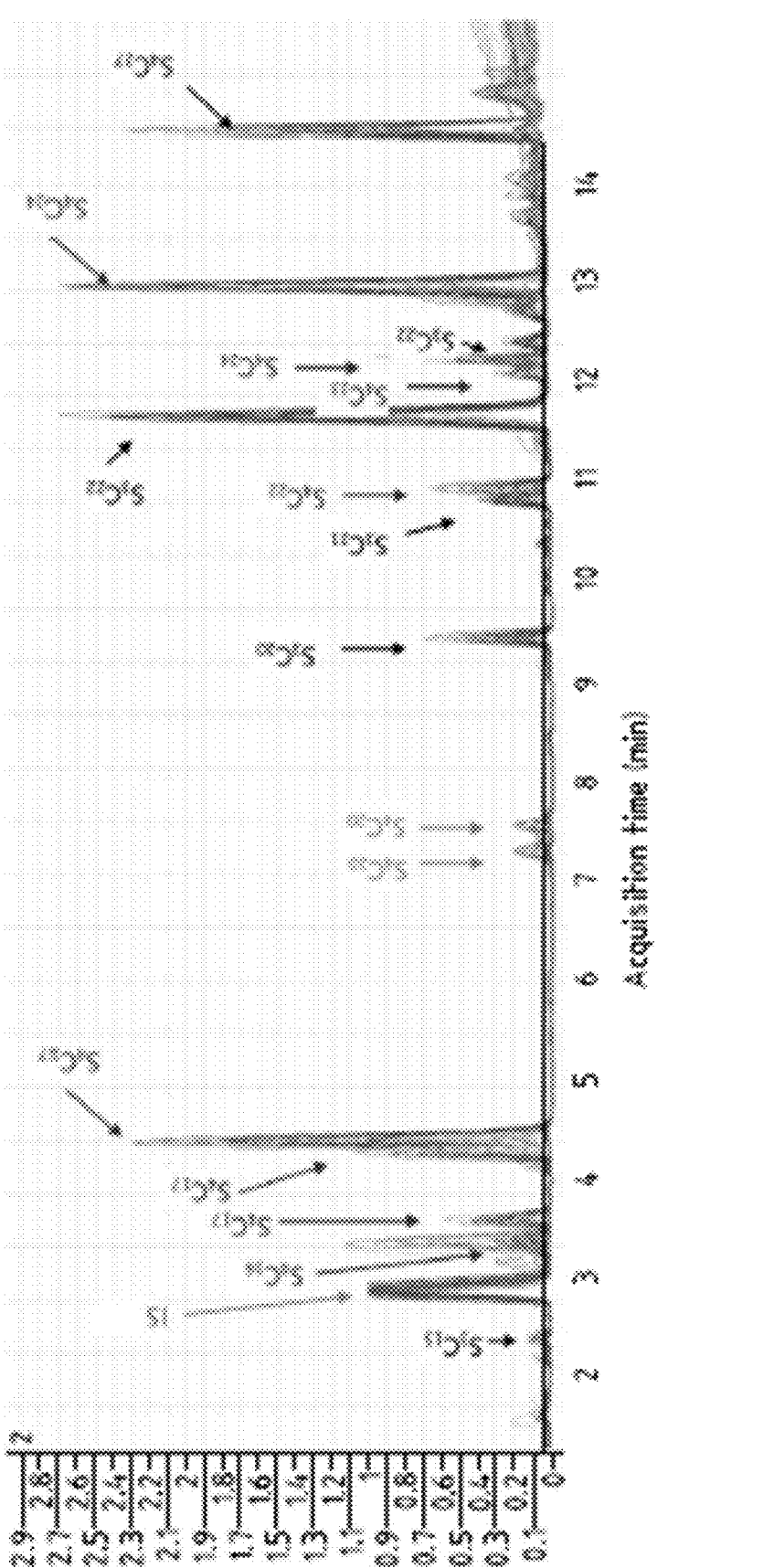

FIG. 3: Shows a LC-MS superimposed chromatogram showing the presence and relative concentrations of various acyl sugars of insect resistant plants (red peaks), intermediate resistant plants (orange peaks), and susceptible plants (greenpeaks). The acyl sugar compounds that are labelled in red are present in high concentrations in plants that are insect resistant and are considered to play a vital role in insect resistance in the plant. The acyl sugars labelled in green are mainly present in susceptible plants. From this analysis, it can be concluded that plants having improved insect resistance is linked to high levels of $C_{29}H_{48}O_{15}$ (S4:C17) and $C_{36}H_{62}O_{15}$ (S4:C24) acyl sugars. Furthermore, no significant changes were observed in the acyl sugar content of $C_{27}H_{46}O_{14}$ (S3:C15), $C_{32}H_{56}O_{14}$ (S3:C20), $C_{33}H_{58}O_{14}$ (S3:C21), $C_{34}H_{60}O_{14}$ (S3:C22) and $C_{39}H_{68}O_{15}$ (S4:C27) in relation to insect resistance of the plants.

FIG. 4: Shows the genomic region (gDNA), coding sequence (cDNA) and protein sequence of the SlAT2 (SEQ ID No. 1 to 3, respectively), and gDNA, cDNA and protein sequence of the AP2e (SEQ ID No. 4 to 6, respectively), wherein SlAT2 in combination with AP2e provides whitefly resistance in tomato plants.

EXAMPLES

Detached Leaves Bioassay

Young leaves of at least 12 weeks old plants (*S. lycopersicum*) of about 4 cm long were detached from the top of approximately 50 tomato plants grown in a plastic greenhouse. Petiole of the leaf was placed into a tube containing a nutritive agarose gel. The tube, with the adaxial part of the leaf side up, was placed (using blu-tack) in horizontal, on the wall of a glass petri dish at medium height, such that the leaf had space between the leaf and the petri dish on both the adaxial and abaxial sides. Each petri dish was then inoculated with 25 whiteflies, which were anaesthetized with $CO_2$ for 3 seconds.

After 24-48 hours, the number of whiteflies in the adaxial or abaxial surface was counted together with the number of dead whiteflies. Each plant was tested twice and the number of whiteflies that were alive (feeding from the adaxial and the abaxial part of the leaf plus the whiteflies still flying around in the petri dish) versus the dead whiteflies were used to calculate the percentage of dead whiteflies. Correlation analysis between specific acyl sucroses and the whitefly mortality revealed that different specific acyl sucrose molecules play a different role in the resistance/susceptibility to whiteflies. As showed in FIG. 2 representing whitefly (WF) mortality versus the specific acyl sucrose content present in the plant, mainly $C_{29}H_{48}O_{15}$ (S4:C17) and $C_{36}H_{62}O_{15}$ (S4:C24) acyl sugars showed have a high impact on resistance. Other acyl sugar compounds that also showed a link with resistance are the $C_{28}H_{46}O_{15}$ (S4:C16), $C_{34}H_{58}O_{15}$ (S4:C22), $C_{35}H_{60}O_{15}$ (S4:C23), $C_{33}H_{56}O_{15}$ (S4:C21), and $C_{37}H_{64}O_{15}$ (S4:C25) acyl sugars.

Liquid Chromatograpy Mass Spectrometry (LC-MS) Analysis Acyl Sugar Content in Tomato A chemical analysis by LC-MS of the leaf surface was performed on a set of tomato plants, including insect resistant tomato plants according to present invention, intermediate resistant plants, and susceptible plants (all *S. lycopersicum*). Plants were grown till 10 side shoots and two opposite leaflets (3×3×3 cm) from the $3^{rd}$ or $4^{th}$ apical leaf were put in a 10 ml glass vial. Two milliliters of methanol with internal standard (Sucrose octaacetate, 10 mg/l) was added and the vial was shaken for 15 seconds. The leaflets were taken out and 300 μl of methanol extract was transferred to an LC-vial and analyzed using an Agilent 1290 Infinity II UHPLC coupled to an Agilent 6230 TOF mass spectrometer.

One μL of extract was injected and separated on an Agilent ZORBAX RRHD Eclipse Plus C18 column at 50° C. with a mobile-phase flow-rate of 0.3 m/min. The mobile phase was comprised of water+0.1% formic acid (A) and acetonitrile+0.1% formic acid (B) in the following A:B gradient; from 60:40 to 45:55 in 6 minutes to 10:90 in 8 minutes to 60:40 in 3 minutes. Molecules were ionised at 325 eV (positive mode) and detected in a range of 50-1500 mu at 1 spectrum/second. The extract comprised mainly of acylsugars that were detected as sodium adducts in the mass spectrometer.

Individual acyl sugars were identified using MassHunter Qualitative Analysis software (Agilent) by calculating the molecular formulas on the basis of the mother ion constituting the chromatographic peaks. Here, molecular formulas were constrained by allowing carbon, hydrogen and oxygen atoms to form the mother ion, in combination with $H^+$, $Na^+$ and $K^+$ and formate adducts to appear, plus a double bond equivalent (DBE) range of 1-10. The exact mass of the mother ion in combination with the DBE allows extrapolation of the basic structure of the acyl sugar molecule; the backbone moiety, number of acyl chains and the total number of carbon atoms forming the acyl chains. Amounts of acylsugars were calculated by using MassHunter Quantitative Analysis Software (Agilent) for chromatogram peak integration and comparing the total peak area of the individual acylsugars to that of the internal standard (sucrose octaacetate).

With the LC-MS corresponding results were obtained as obtained with the detached leaves bioassay as described above. Further evidence that specific acyl sugars are involved in the insect resistance can be derived from the LC-MS chromatogram plot, FIG. 3. The individual chromatograms of methanolic leaf dips of insect resistant plants (red), intermediate resistant plants (orange), and susceptible plants (green) were superimposed. The acyl sugar compounds that are labelled in red are present in high concentrations in plants that showed to be highly resistant to whiteflies. In contrast in plants that showed to be susceptible to whitefly, no or only low concentrations of these specific acyl sugars were detected by LC-MS. Furthermore, in respect to the whitefly susceptible plants the acyl sugars that were mainly present are labelled in green, and remarkably were not, or at low concentrations, present in the resistant plants. From this analysis, it can be concluded that plants having improved insect resistance is linked to high $C_{29}H_{48}O_{15}$ (S4:C17) and $C_{36}H_{62}O_{15}$ (S4:C24) acyl sugars. No significant changes were observed in the acyl sugar content of $C_{27}H_{46}O_{14}$ (S3:C15), $C_{32}H_{56}O_{14}$ (S3:C20), $C_{33}H_{58}O_{14}$ (S3:C21), $C_{34}H_{60}O_{14}$ (S3:C22) and $C_{39}H_{68}O_{15}$ (S4:C27) in insect susceptible and resistant plants.

Genotypic Analysis, Mapping of SlAT2 and AP2e.

The production of acyl sugars in tomato plants is linked with high levels of insect resistance in the plant. Important is to know which type of acyl sugars are needed for insect resistance. Looking into genotypic data on the resistant tomato plant population (*S. lycopersicum*) by marker analysis, marker M8 and M5 (Table 1) were used to identify the QTLs that clearly correlate with the production of $(C_{36}H_{62}O_{15})$ (S4:C24) and $(C_{29}H_{48}O_{15})$ (S4:C17) acyl sucrose.

Briefly, genomic regions that are linked to the amount of acyl sugars which are produced by type IV trichomes have been mapped on chromosome 6, based on the reference genome SL2.40. It was determined that the region involved in acyl sugar production linked to insect resistance is located between positions 43250794 bp and 43259933 bp. Marker M5 is 100% linked with the amount of acyl sugars (Table 1) being produced. Based on the reference genome SL2.40 and in silico prediction analysis (ITAG 2.3), one gene Solyc06g075510.2 is located in the fine mapped region that encodes for an APETALA2 ethylene-responsive transcription factor (AP2e).

Furthermore, the type of acyl sugars is crucial for providing the whitefly resistance in tomato plants. It was observed that plants comprising the AP2e gene and producing acyl sugars are not always resistant for whitefly. Comparing the acyl sugar profiles of the susceptible and resistant plants, it was concluded that plants having improved insect resistance are linked to high levels of tetra-acyl (S4) sucroses $C_{29}H_{48}O_{15}$ (S4:C17) and $C_{36}H_{62}O_{15}$ (S4:C24) in comparison to susceptible plants that mostly accumulate tri-acyl sucroses (S3). Marker M8 is 100% linked with the type of acyl sugars (Table 1), and one specific sequence was mapped on chromosome 1, which encoded a member of the BAHD family of acyltransferases, more specifically an acetyl-CoA-dependent acyltransferase enzyme SlAT2, capable of acyl sucrose acetylation and responsible for the production of $C_{29}H_{48}O_{15}$ (S4:C17) and $C_{36}H_{62}O_{15}$ (S4:C24).

Sequencing of the functional SlAT2 gene resulted in a genomic sequence including promotor region (SEQ ID No. 1). Plants comprising SEQ ID No. 1, i.e. a functional SlAT2, in combination with AP2e have an increased S4/S3 ratio and are highly resistant to whitefly compared to the plants without SEQ ID No. 1, these plants are not capable to produce S4 sugars which results in susceptibility to whitefly. SEQ ID No. 1 shows the genomic sequence comprising the SlAT2 gene including promotor region of the whitefly resistant plant of present invention. SEQ ID No. 2 shows the coding sequence of SlAT2 in the plant of present invention that encodes for the SlAT2 protein of SEQ ID No. 3. SEQ ID No. 4 shows the genomic sequence of the AP2e gene including promotor region of the whitefly resistant plant of present invention. SEQ ID No. 5 shows the coding sequence of AP2e in the plant of present invention that encodes for the AP2e protein of SEQ ID No. 6.

TABLE 1

| Marker sequences used for QTL mapping | |
| --- | --- |
| Marker | Sequence |
| M5_F (SEQ ID No. 7) | GCGAGGCATTTGTTGAAGTTGC TAATGC |
| M5_R (SEQ ID No. 8) | GGTTGATACAAACAGCCCATTG |
| M8_F (SEQ ID No. 9) | AAGCAATGCGAAATATCGTAAC |
| M8_R (SEQ ID No. 10) | GAGAGACCCTCACATTTTGTC |

It was found that the SlAT2 in combination with the AP2e gene specifically promotes and regulates the production of specific types of acyl sugars like $C_{29}H_{48}O_{15}$ (S4:C17 acyl sucrose) and/or $C_{36}H_{62}O_{15}$ (S4:C24 acyl sucrose) and more in general increases the ration between tetra- (S4) and tri-acylated (S3) sugar. The combination AP2e (marker M5)+SlAT2 (marker M8) increases the level of S4:C17 and S4:C24 acyl sucrose that is needed for whitefly resistance. Several tomato plants were selected for their presence of AP2e gene and the presence/absence of SlAT2 gene, homo/heterozygous using the M5 and M8 markers. Total acyl sugars content (g per gram plant fresh weight (gFW) per plant was determined, as well as the presence of specifically specific acyl sugars $C_{29}H_{48}O_{15}$ (S4:C17 acyl sucrose) and $C_{36}H_{62}O_{15}$ (S4:C24 acyl sucrose), the ratio between tetra- (S4) and tri-acylated (S3) sucroses, and the resistance to whitefly. The genotypes of SlAT2 are co-segregating with the production of S4:C17 and S4:C24 acyl sucrose and increased S4/S3 ratio, and is linked with the white fly resistance level, see Table 2.

TABLE 2

| | | | AP2e, SlAT2 presence in plants and the effect on Acyl sugars and whitefly resistance. | | | |
| --- | --- | --- | --- | --- | --- | --- |
| Plant | AP2e (M5) | SlAT2 (M8) | Total AcS (µg/gFW) | Sum S4C17 + S4C24 (µg/gFW) | Ratio S4:S3 AcS | WF resistance % |
| 1. | b | b | 1038.7 | 479.7 | 1.46 | 60 |
| 2. | b | b | 1503.8 | 551.9 | 2.33 | 49 |
| 3. | b | b | 1060.5 | 431.5 | 1.67 | 44 |
| 4. | b | a | 823.1 | 9.6 | 0.05 | 21 |
| 5. | b | a | 579.8 | 5.6 | 0.33 | 7 |
| 6. | b | a | 1872.4 | 12.6 | 0.33 | 22 |
| 7. | b | b | 1735.8 | 544.3 | 1.95 | 74 |
| 8. | b | h | 1316.5 | 350.4 | 1.12 | 60 |
| 9. | b | h | 1820.4 | 632.2 | 1.87 | 45 |
| 10. | b | a | 2090.5 | 59.4 | 0.48 | 30 |
| 11. | b | a | 1180.0 | 28.7 | 0.57 | 21 | a = absent
b = present
h = heterozygous

The invention claimed is:

1. A tomato plant having improved whitefly resistance, wherein said plant comprises a combination of an acetyl-CoA-dependent acyltransferase gene (SlAT2) encoding a cDNA sequence having at least 99% sequence identity with SEQ ID No. 2, and an APETALA2e ethylene-responsive transcription factor gene (AP2e) encoding a cDNA sequence of SEQ ID No. 5, wherein said combination of SlAT2 and AP2e genes result in an increased $C_{29}H_{48}O_{15}$ and $C_{36}H_{62}O_{15}$ acyl sugar content as compared to a tomato plant not comprising said combination of genes.

2. The tomato plant according to claim 1, wherein said tomato plant comprises tetra-acyl (S4) sugar and tri-acyl (S3) sugars, wherein a ratio between tetra-acyl (S4) sugars and tri-acyl (S3) sugars (S4:S3) in the tomato plant is at least 1.

3. The tomato plant according to claim 1, wherein the genomic region encoding the SlAT2 gene comprises SEQ ID No.1 and wherein the genomic region encoding the AP2e gene comprises SEQ ID No.4.

4. The tomato plant according to claim 1, wherein the SlAT2 gene encodes for the protein sequence represented by SEQ ID No. 3, and wherein the AP2e gene encodes for the protein sequence represented by SEQ ID No. 6.

5. The tomato plant according to claim 1, wherein the acyl sugar content of $C_{29}H_{48}O_{15}$ is at least 150 µg/g of fresh weight (FW) of plant leaves, and/or wherein the acyl sugar content of $C_{36}H_{62}O_{15}$ is at least 125 µg/g of FW of plant leaves.

6. The tomato plant according to claim 1, wherein the plant furthermore has an increased acyl sugar content of one or more selected from the group consisting of $C_{28}H_{46}O_{15}$, $C_{34}H_{58}O_{15}$ and $C_{35}H_{60}O_{15}$ as compared to a tomato plant not comprising said combination of genes.

7. The tomato plant according to claim 1, wherein the acyl sugar content of $C_{28}H_{46}O_{15}$ is at least 10 µg/g of FW of plant leaves and/or wherein the acyl sugar content of $C_{34}H_{58}O_{15}$ is at least 15 µg/g of FW of plant leaves, and/or wherein the acyl sugar content of $C_{35}H_{60}O_{15}$ is at least 12.5 µg/g of FW of plant leaves.

8. The tomato plant according to claim 1, wherein the plant is obtainable from deposit NCIMB 43748.

9. The tomato plant according to claim 1, wherein the plant is furthermore resistant to mites.

10. A seed, a fruit, or a plant part of the tomato plant according to claim 1, wherein said seed, fruit, or plant part comprises a combination of an acetyl-CoA-dependent acyl-transferase gene (SlAT2) encoding a cDNA sequence having at least 99% sequence identity with SEQ ID No. 2, and an APETALA2e ethylene-responsive transcription factor gene (AP2e) encoding a cDNA sequence of SEQ ID No. 5.

11. A method for providing a tomato plant having improved whitefly resistance comprising the steps of:

providing a whitefly susceptible tomato plant; and mutating its genome by introducing therein a combination of an acetyl-CoA-dependent acyltransferase gene (SlAT2) encoding a cDNA sequence-having at least 99% sequence identity with SEQ ID No. 2, and an APETALA2e ethylene-responsive transcription factor gene (AP2e) encoding a cDNA sequence of SEQ ID No. 5, wherein said combination of SlAT2 and AP2e genes result in an increased $C_{29}H_{40}s15$ and $C_{36}H_{62}O$ is acyl sugar content as compared to a tomato plant not comprising said combination of genes.

12. A method for providing a tomato plant having improved whitefly resistance, wherein the method comprises the steps of:

a) crossing a tomato plant that is susceptible to whitefly with the tomato plant according to claim 1; and b) selecting *S. lycopersicum* plants having improved insect resistance that comprise the SlAT2 gene and AP2e gene.

13. The method according to claim 12, wherein the selection of *S. lycopersicum* plants having improved insect resistance is by determination of $C_{29}H_{48}O_{15}$ and/or $C_{36}H_{62}O_{15}$ acyl sugar content, wherein the acyl sugar content of $C_{29}H_{48}O_{15}$ is at least 150 μg/g of fresh weight (FW) of plant leaves and/or wherein the acyl sugar content of $C_{36}H_{62}O_{15}$ is at least 125 μg/g of fresh weight (FW) of plant leaves.

14. A composition comprising a combination of two genomic regions for providing insect resistance in tomato plants, wherein one genomic region comprising SEQ ID No. 1 that encodes an acetyl-CoA-dependent acyltransferase gene (SlAT2) and a second genomic region comprising SEQ ID No. 4 that encodes an APETALA2e ethylene-responsive transcription factor gene (AP2e).

15. A composition comprising a combination of two genes for providing insect resistance in tomato plants, wherein one gene encodes an acetyl-CoA-dependent acyltransferase (SlAT2) protein comprising SEQ ID No. 3 and a second gene that encodes an APETALA2e ethylene-responsive transcription factor (AP2e) comprising SEQ ID No. 6.

16. The tomato plant according to claim 1, wherein said tomato plant comprises tetra-acyl (S4) sugar and tri-acyl (S3) sugars, wherein a ratio between tetra-acyl (S4) sugars and tri-acyl (S3) sugars (S4:S3) in the tomato plant is at least 1.7.

17. The tomato plant according to claim 1, wherein the tomato plant is furthermore resistant to spider mites.

* * * * *

SEQUENCE LISTING

<160> NUMBER OF SEQ ID NOS: 10

<210> SEQ ID NO 1

<211> LENGTH: 2322
<212> TYPE: DNA
<213> ORGANISM: Solanum lycopersicum
<220> FEATURE:
<223> OTHER INFORMATION: gDNA SlAt2

<400> SEQUENCE: 1

```
tcacttgtag gggtggaaaa atagactaaa cctatatata tattatatta tatggttata      60
agtttgatta atccatttta aaatggtttt gtcgttcgaa taaaaatgaa taaaatataa     120
attaattctg gttacattcg tcaaatataa atatatatat tttttaatta agatattatt     180
tttaataaac acttaaaaat tcttcaaaat aattggattg attattaccc aatttattat     240
ttagcgaaga tattgtataa taagaaaaga cttactttca gagtaacttt cttttatctc     300
caaaggaaaa ggcttggttg aaggcaaaat ttgatgtaat tttggaattc cggcatgcaa     360
agttacaaga gtttcacaca ataatgctaa ttattgtagg aatggcttta tcccaagaca     420
aaatgagtcc aaatgagttt tcactttccc aatcaaggac attctagttc gacatgctac     480
tttcacattc tcaatttatt tttaaatatt tgatagatga gtgaaactta attttcgatt     540
tttagttagt gagtaaattt tctctcagaa tagttttggt tatgaggaga aataaattta     600
taaactctat tgaaaatatt gtttggaatt ttaggtttct agtttataaa gtatttccca     660
tgtttggtgc caaaatcaag aacaaccttt tgccaagaaa atgcaacagg taatatatag     720
cgacatttga ctgatatgat ttaaaatatt taccctgaaa attttgtaat tgtaaaaact     780
tttagcgtaa ttaaccgccc aaataaattc tgtagtatat acactagtgt ttgttctgaa     840
caatgcactt tatgaatgtt aaatgcaata tattaaagat tgacgccatg ccaaactata     900
tatataatag gaatgaacat tgatagattt attcagaaac aacactttat tcatccaaaa     960
aaaaagatga attgttatat tgaaattcaa tcaaggaaaa tggtgaaacc ctcagctcct    1020
accccggata atcttcggag attgaagctt tccttgttcg atcagatgga tattggtgca    1080
tatgtaccaa ttgtcttcaa ctacttgccg aacagcactt catcatatga tcatgatgat    1140
aagcttgaaa aatcattgtc ggagacgcta accaagtttt acccttttgc tggaagattt    1200
agaaaaggca ttgatccatt ttccatcgac tgcaatgatg aaggtattga atatgttcga    1260
accaaagtca atgcagacga tcttgcccaa tatctccgtg gtcaagccca taatgatatt    1320
gagtcgtctt tgattgatct tcttcctgta atgcatcgtc taccatcaag tccattattt    1380
ggtgttcaag tgaatgtatt caataacgga ggtgtaacca tagggataca aattttacat    1440
atggtatctg atgctttcac tttagtaaaa tttgtaaatg aatgggcgca caccaccctt    1500
acagggacga tgccactaga taatcccggt tttggtcaat tgccatggct atttccagca    1560
agagcgctac cgtttccatt acctgatttc aacactacta ctgcccctaa ttataagaat    1620
gttacaaaga ggtttctctt tgatgctttg gcaatagaaa acctcagaaa tacaatcaaa    1680
gccaatgaca tgatgatgaa gcaaccttct agagtggtgg tcgtgatgtc cctaatatgg    1740
aaggttctta cacacatttc ttccgccaaa aataatggaa attcaaggga ctcatcttta    1800
gtgtttgttg ttaatttgag gggaaaactg tcatgtactg caccgtcttt agaacacgtt    1860
gtagggaatt gtgtaatacc agcaactgct aacaaggagg cgatgaggc aagaagaaag    1920 gatgatgagt tgaatgattt cgttaagttg gtaagaaata caatacggga cacatgtgaa    1980
gccattggta aggcggaaag cgttgatgat atttcctctt tagcatttaa caatctgacg    2040
aaatgtatag aaaaaattct gcatggagac gagatgggact tctattcgtg ctctagttgg    2100
tgcggattcc cttggtatga agctgacttt ggttggggaa agccattctg ggtgagctca    2160
```

-continued

```
gttagttttg gtcatcatgg agtaactaat ctcatggaca caaaagatgg tgatggaata      2220
caagtaacaa tttgtttgaa ggagaatgac atgattgagt ttgagagaga ccctcacatt      2280
ttgtcctcca cttcaaaact agcattccat tccttaggat aa                        2322
```

```
<210> SEQ ID NO 2
<211> LENGTH: 1356
<212> TYPE: DNA
<213> ORGANISM: Solanum lycopersicum
<220> FEATURE:
<223> OTHER INFORMATION: cDNA SlAt2

<400> SEQUENCE: 2
```

```
atgaattgtt atattgaaat tcaatcaagg aaaatggtga aaccctcagc tcctaccccg        60
gataatcttc ggagattgaa gctttccttg ttcgatcaga tggatattgg tgcatatgta       120
ccaattgtct tcaactactt gccgaacagc acttcatcat atgatcatga tgataagctt       180
gaaaaatcat tgtcggagac gctaaccaag ttttacccct ttgctggaag atttagaaaa       240
ggcattgatc cattttccat cgactgcaat gatgaaggta ttgaatatgt tcgaaccaaa       300
gtcaatgcag acgatcttgc ccaatatctc cgtggtcaag cccataatga tattgagtcg       360
tctttgattg atcttcttcc tgtaatgcat cgtctaccat caagtccatt atttggtgtt       420
caagtgaatg tattcaataa cggaggtgta accataggga tacaaatttt acatatggta       480
tctgatgctt tcactttagt aaaatttgta aatgaatggg cgcacaccac ccttacaggg       540
acgatgccac tagataatcc cggtttttggt caattgccat ggctatttcc agcaagagcg       600
ctaccgtttc cattacctga tttcaacact actactgccc ctaattataa gaatgttaca       660
aagaggtttc tctttgatgc tttggcaata gaaaacctca gaaatacaat caaagccaat       720
gacatgatga tgaagcaacc ttctagagtg gtggtcgtga tgtccctaat atggaaggtt       780
cttacacaca tttcttccgc caaaaataat ggaaattcaa gggactcatc tttagtgttt       840
gttgttaatt tgaggggaaa actgtcatgt actgcaccgt ctttagaaca cgttgtaggg       900
aattgtgtaa taccagcaac tgctaacaag gagggcgatg aggcaagaag aaaggatgat       960
gagttgaatg atttcgttaa gttggtaaga aatacaatac gggacacatg tgaagccatt      1020
ggtaaggcgg aaagcgttga tgatatttcc tctttagcat ttaacaatct gacgaaatgt      1080
atagaaaaaa ttctgcatgg agacgagatg gacttctatt cgtgctctag ttggtgcgga      1140
ttcccttggt atgaagctga ctttggttgg ggaaagccat tctgggtgag ctcagttagt      1200
tttggtcatc atggagtaac taatctcatg gacacaaaag atggtgatgg aatacaagta      1260
acaatttgtt tgaaggagaa tgacatgatt gagtttgaga gagaccctca cattttgtcc      1320
tccacttcaa aactagcatt ccattcctta ggataa                              1356
```

```
<210> SEQ ID NO 3
<211> LENGTH: 451
<212> TYPE: PRT
<213> ORGANISM: Solanum lycopersicum
<220> FEATURE:
<223> OTHER INFORMATION: Protein SlAT2

<400> SEQUENCE: 3
```

```
Met Asn Cys Tyr Ile Glu Ile Gln Ser Arg Lys Met Val Lys Pro Ser
1               5                   10                  15

Ala Pro Thr Pro Asp Asn Leu Arg Arg Leu Lys Leu Ser Leu Phe Asp
            20                  25                  30
```

```
Gln Met Asp Ile Gly Ala Tyr Val Pro Ile Val Phe Asn Tyr Leu Pro
    35              40              45

Asn Ser Thr Ser Ser Tyr Asp His Asp Asp Lys Leu Glu Lys Ser Leu
    50              55              60

Ser Glu Thr Leu Thr Lys Phe Tyr Pro Phe Ala Gly Arg Phe Arg Lys
65              70              75              80

Gly Ile Asp Pro Phe Ser Ile Asp Cys Asn Asp Glu Gly Ile Glu Tyr
                85              90              95

Val Arg Thr Lys Val Asn Ala Asp Asp Leu Ala Gln Tyr Leu Arg Gly
            100             105             110

Gln Ala His Asn Asp Ile Glu Ser Ser Leu Ile Asp Leu Leu Pro Val
        115             120             125

Met His Arg Leu Pro Ser Ser Pro Leu Phe Gly Val Gln Val Asn Val
    130             135             140

Phe Asn Asn Gly Gly Val Thr Ile Gly Ile Gln Ile Leu His Met Val
145             150             155             160

Ser Asp Ala Phe Thr Leu Val Lys Phe Val Asn Glu Trp Ala His Thr
                165             170             175

Thr Leu Thr Gly Thr Met Pro Leu Asp Asn Pro Gly Phe Gly Gln Leu
            180             185             190

Pro Trp Leu Phe Pro Ala Arg Ala Leu Pro Phe Pro Leu Pro Asp Phe
            195             200             205

Asn Thr Thr Thr Ala Pro Asn Tyr Lys Asn Val Thr Lys Arg Phe Leu
    210             215             220

Phe Asp Ala Leu Ala Ile Glu Asn Leu Arg Asn Thr Ile Lys Ala Asn
225             230             235             240

Asp Met Met Met Lys Gln Pro Ser Arg Val Val Val Met Ser Leu
            245             250             255

Ile Trp Lys Val Leu Thr His Ile Ser Ser Ala Lys Asn Asn Gly Asn
            260             265             270

Ser Arg Asp Ser Ser Leu Val Phe Val Val Asn Leu Arg Gly Lys Leu
    275             280             285

Ser Cys Thr Ala Pro Ser Leu Glu His Val Val Gly Asn Cys Val Ile
    290             295             300

Pro Ala Thr Ala Asn Lys Glu Gly Asp Glu Ala Arg Arg Lys Asp Asp
305             310             315             320

Glu Leu Asn Asp Phe Val Lys Leu Val Arg Asn Thr Ile Arg Asp Thr
                325             330             335

Cys Glu Ala Ile Gly Lys Ala Glu Ser Val Asp Asp Ile Ser Ser Leu
            340             345             350

Ala Phe Asn Asn Leu Thr Lys Cys Ile Glu Lys Ile Leu His Gly Asp
            355             360             365

Glu Met Asp Phe Tyr Ser Cys Ser Ser Trp Cys Gly Phe Pro Trp Tyr
    370             375             380

Glu Ala Asp Phe Gly Trp Gly Lys Pro Phe Trp Val Ser Ser Val Ser
385             390             395             400

Phe Gly His His Gly Val Thr Asn Leu Met Asp Thr Lys Asp Gly Asp
                405             410             415

Gly Ile Gln Val Thr Ile Cys Leu Lys Glu Asn Asp Met Ile Glu Phe
            420             425             430

Glu Arg Asp Pro His Ile Leu Ser Ser Thr Ser Lys Leu Ala Phe His
    435             440             445

Ser Leu Gly
```

450

<210> SEQ ID NO 4
<211> LENGTH: 4556
<212> TYPE: DNA
<213> ORGANISM: Solanum lycopersicum
<220> FEATURE:
<223> OTHER INFORMATION: gDNA AP2e

<400> SEQUENCE: 4

```
aatgaaaaaa caaaagggaa atgtcataga ttttctatac gaataattgc tattacttgt        60
aattagaagt gacattgcgg gagtaagcta aataaaatat gtatataact atataaattt       120
tgtacaaaat aggaccgaat tttagtccaa aactgtaaat gaagagtgtt tttataaatt       180
ataaatgttt ggataattta aaattttaaa aaatccccga atactttttc ccccctaata       240
tttgaaaact taggatggtt accaaatatg tttataaaga aataacaact tatatttgaa       300
aatacttgtg gccaaatgaa aatgagaaac tcgtttttt aaaatttcta tatgtaaaat       360
ttaaaaatgt aattttttac caaaatattt tcatcgtcca taatgcaccc gcagtctttt       420 gtaaataag gtccacttga aacgaaaagc tcacggccca tgcaaacctc ctgcatcata       480
cattagttaa ttagtatact taatttcaaa cttatttatc ttagtttact ttgagtttta       540
aattttgatt tttatataca aaattatgat gttaaattta aaatatatca aatactttcc       600
tattctgttt tataatgtct acaatgagat ctttaataaa aaaagaaatt ttattttttt       660
ggtccatatc aaattatgat ttttttgaaa ccattatgct aagttaaact acaatttaac       720
tgataactaa tcaatcctca agggaactat tcattcggac ccatctagga atccattatt       780
cgttagccat ttacaagaat agagacccca ttaagaataa tacataaaat taatagttat       840
aatggagcac ccaatacttc ttaatttgca taaaaggtgc ttgcttgatt ttcaatttcc       900
taaaagagat atatataatg taggtgaaga aaataatctt tcctaattgc cagcgtggat       960
tcaaatgagt aattaaaaat taaataaaata aacataaata tagattatac aacaaaatga      1020 aaagggggc cccacgttct gttttggta aagaaataa gagtaatttt ttgtaaattt      1080
ttccatataa aaccatagtg tttcccaaaa taagaggaac caaaagtagc ttcacaaatc      1140
acacaaccca cataagttgc ctcacacgtc ccatctttct tcttccccaa cccctacccc      1200
ctatctactg ctcctatgga gtactataac taaatgaaat tcatctcaat ttattcttct      1260
tccattgacg cttacaatca ttttggttaa ctcccacaga tattttatag ttagtcaaaa      1320
acagaacaat gttggatctc aatgtaagcg taatctacag taatgacctt ccacaagttt      1380
ctctacttga tgaatcagcc acctccaatt catccttacg aaatgcggaa gctacaacca      1440
gtgccggtga cgaagattcg tgcgccggtg agttgttcgc tttcaatttt ggaatcctca      1500
aagttgaagg agctgagact agtaggagca gcaacaacga tgatgaggaa gcatacggta      1560
agaatcagag agttactcat tctcaattcg tgactaggca gctgtttccc gttgatgatg      1620
gtgagttgaa ccggaaacaa accgatcggg tcattctctc ctccgctcga tccggtactt      1680
ctatcggttt tggagatgtg cggataatac aacagcaaca aacggagcaa ccgaaacaac      1740
aagtgaagaa gagtaggaga ggcccaaggt caagaagttc acagtacaga ggtgtcactt      1800
tctaccgtag aactggtaga tgggaatcac atatatggtt agttttctaa ctgatttttt      1860
ttttgttgat aggatgatga ttaattggca aatgataaat tgtcaatttt attaatataa      1920
ctacaattgg atgcagggac tgtgggaaac aagtatattt gggtatggat attgctattt      1980
taaatataca gtttggttaa tttcgttgtt tttgtggatt ttggtgctaa agctgtgtct      2040
```

-continued

```
atactttttg ctaatttttg attgttttt  tttgttgctt tatattaggt ggtttgata   2100 ctgctcacac agcagcaagg taaaataaaa gtcatatgag ttctcaaata tacgcgtcat   2160 cagattttc  aaatttatgc tatttcccaa atttgattgt atttgttttc ttctccgttg   2220
tacagagctt atgacagagc tgcaattaaa tttaggggtg ttgatgctga tatcaacttt   2280
agcttaagtg attacgagga ggatatgcaa caggttagaa atgcaaagat ttaatatgtg   2340
caaatatgtt aaagtcactg ttgagcgctt ctctgggttt attattgctt ctgttttaat   2400
tggcatcaat aatatgaatc atatacaagt attctgaact atttggtgga cacctttttt   2460
tgatttacgc agatgaaaaa ccttggtaaa gaagaatttg tgcacttgct gcgacgccat   2520
agcactggtt tctcaagagg gagctccaaa ttcagaggag tgacgctaca taaatgtggc   2580
agatgggagg ctcggatggg acagttcctc gggaaaaagt aaggaactca ctcactcatt   2640
gaaattctcg aagaagtaga ttacatctta ttatagtaat tggtcaaaaa tgggacatac   2700
atatgtttaa attgcgtatt tgaagaagaa atcattggga caacagtatt catagtgggg   2760
attgcactgc ttatattgca ggtatatata tcttgggctg ttcgacagcg aagtagaagc   2820
tgcaaggtcc taatgataat gaattaccct ctctctgatg atgaacattt atcctaaatt   2880
ttcaacttta attatgtgtc atctaaccgg tatctccttt attttttgc aaatcagggc   2940 ctacgataag gcggcaatta aaactagcgg aagggaagct gttaccaact ttgagccaag   3000
tagctatgaa ggggaaacaa tgtctttacc acagagtgaa ggtttgctca aaagttcttg   3060
gtcatttcca aactaatata gatacatgca acagtagtat ctatatgtgg atctatctca   3120
tttgtgatgc ctatgatgca ggtagccaac atgatcttga tctgaacttg gggatatcga   3180
ccacttcttc aaaggaaaat gacaggttgg gaggttctcg ctatcatcct tacgatatgc   3240
aagacgcaac aaaacctaag gtattagcag agtagcttat atgcttctgt tcttgcaaaa   3300
tcaattggat taaaatgctc tcctttatgt tatagtcttc tattgttact tctttcatag   3360
ataatatgca agagatctat tgcagtaatt catgagtatt agttattggt agtaatataa   3420
tctccttttt gttaatttag atagcttttc ccattcatac ataattgtga taaaacatgt   3480
tcatgagcat tgttaatctt tcgttttgt agattgtaat aatctatttg tgctctttaa   3540
ctatagatgg ataaacctgg ttcagtaata gttggaagtt cacatctcaa gggactatca   3600
atgtcgtccc aacaagctca attgtggact ggaatctatt ctaatttctc ttccagctat   3660
gaggtaaaat actaactcta ccatcagtca gaaatttggg accaaataca gtgatgaaac   3720
tccaatttat ctctgtttag tcttcttttc ctcacttatc gtcaaattag cacgtattca   3780
gttgccaaaa tagccatatt catgcccct  taccccaatt tccctcaagt gctgggacca   3840
tttgtgttgt atgaaatgtt ttaccttttt ccttctagtt ctttgcattg tcttcagttg   3900
ccaaaataac tatctccatc cccgaagccc aatttctctg aagtactgaa attatttgtc   3960
ttgtatgaaa cattttacct ttttacttct tgtgtttttt ggggctgata atcagtgata   4020
gtatgcccca tgacaaatga taatattgtt gtgggatcgt acaccccatg ataagattta   4080
tctttaactt aacaaaattt ctttgtactt agtcaatcat ttggataatc atgagctatg   4140
ttatacttgg ggtgcatatt ctcatgtgtg gtcacagcca gttttcact  gcaaacagtt   4200 gtctaaaagt caatgtcttt gttatgccct tttgtgcctc ttcttaattg aatgcatcct   4260
tagtgtaacc ttccaaaacc ctctctctgt taatttaact aataatcata tggcagggaa   4320
gagcatatga caagagaaag gacacaggtt catcacaagg acctccaaat tgggcattgc   4380
```

-continued

```
aaatgcctag tcaggttgat acaaacagcc cattgacaat gttctgcacg gcatcatcat    4440
caggattctt cattccatct actacttctg tcacttcatc aacatctgca ttagcaactt    4500
caacaaatgc ctcgcagtgc ttttaccaga ttaatccccg cctaccactt ccataa       4556

<210> SEQ ID NO 5
<211> LENGTH: 1425
<212> TYPE: DNA
<213> ORGANISM: Solanum lycopersicum
<220> FEATURE:
<223> OTHER INFORMATION: cDNA AP2e

<400> SEQUENCE: 5
atgttggatc tcaatgtaag cgtaatctac agtaatgacc ttccacaagt ttctctactt     60
gatgaatcag ccacctccaa ttcatcctta cgaaatgcgg aagctacaac cagtgccggt    120
gacgaagatt cgtgcgccgg tgagttgttc gctttcaatt ttggaatcct caaagttgaa    180
ggagctgaga ctagtaggag cagcaacaac gatgatgagg aagcatacgg taagaatcag    240
agagttactc attctcaatt cgtgactagg cagctgtttc ccgttgatga tggtgagttg    300
aaccggaaac aaaccgatcg ggtcattctc tcctccgctc gatccggtac ttctatcggt    360
tttggagatg tgcggataat acaacagcaa caaacggagc aaccgaaaca caagtgaag     420 aagagtagga gaggcccaag gtcaagaagt tcacagtaca gaggtgtcac tttctaccgt    480
agaactggta gatgggaatc acatatatgg gactgtggga aacaagtata tttgggtggt    540
tttgatactg ctcacacagc agcaagagct tatgacagag ctgcaattaa atttaggggt    600
gttgatgcta tatcaacttt agcttaagt gattacgagg aggatatgca acagatgaaa     660
aaccttggta agaagaatt tgtgcacttg ctgcgacgcc atagcactgg tttctcaaga     720
gggagctcca aattcagagg agtgacgcta cataaatgtg gcagatggga ggctcggatg    780
ggacagttcc tcgggaaaaa gtatatatat cttgggctgt tcgacagcga agtagaagct    840
gcaagggcct acgataaggc ggcaattaaa actagcggaa gggaagctgt taccaacttt    900
gagccaagta gctatgaagg ggaaacaatg tctttaccac agagtgaagg tagccaacat    960
gatcttgatc tgaacttggg gatatcgacc acttcttcaa aggaaaatga caggttggga   1020
ggttctcgct atcatcctta cgatatgcaa gacgcaacaa aacctaagat ggataaacct   1080
ggttcagtaa tagttggaag ttcacatctc aagggactat caatgtcgtc ccaacaagct   1140
caattgtgga ctggaatcta ttctaatttc tcttccagct atgagggaag agcatatgac   1200
aagagaaagg acacaggttc atcacaagga cctccaaatt gggcattgca aatgcctagt   1260
caggttgata caaacagccc attgacaatg ttctgcacgg catcatcatc aggattcttc   1320
attccatcta ctacttctgt cacttcatca acatctgcat tagcaacttc aacaaatgcc   1380
tcgcagtgct tttaccagat taatccccgc ctaccacttc cataa                    1425

<210> SEQ ID NO 6
<211> LENGTH: 474
<212> TYPE: PRT
<213> ORGANISM: Solanum lycopersicum
<220> FEATURE:
<223> OTHER INFORMATION: Protein AP2e

<400> SEQUENCE: 6

Met Leu Asp Leu Asn Val Ser Val Ile Tyr Ser Asn Asp Leu Pro Gln
1                5                  10                  15

Val Ser Leu Leu Asp Glu Ser Ala Thr Ser Asn Ser Ser Leu Arg Asn
            20                  25                  30
```

-continued

```
Ala Glu Ala Thr Thr Ser Ala Gly Asp Glu Asp Ser Cys Ala Gly Glu
        35              40              45

Leu Phe Ala Phe Asn Phe Gly Ile Leu Lys Val Glu Gly Ala Glu Thr
    50              55              60

Ser Arg Ser Ser Asn Asn Asp Asp Glu Glu Ala Tyr Gly Lys Asn Gln
65              70              75              80

Arg Val Thr His Ser Gln Phe Val Thr Arg Gln Leu Phe Pro Val Asp
            85              90              95

Asp Gly Glu Leu Asn Arg Lys Gln Thr Asp Arg Val Ile Leu Ser Ser
            100             105             110

Ala Arg Ser Gly Thr Ser Ile Gly Phe Gly Asp Val Arg Ile Ile Gln
            115             120             125

Gln Gln Gln Thr Glu Gln Pro Lys Gln Gln Val Lys Lys Ser Arg Arg
        130             135             140

Gly Pro Arg Ser Arg Ser Ser Gln Tyr Arg Gly Val Thr Phe Tyr Arg
145             150             155             160

Arg Thr Gly Arg Trp Glu Ser His Ile Trp Asp Cys Gly Lys Gln Val
            165             170             175

Tyr Leu Gly Gly Phe Asp Thr Ala His Thr Ala Ala Arg Ala Tyr Asp
            180             185             190

Arg Ala Ala Ile Lys Phe Arg Gly Val Asp Ala Asp Ile Asn Phe Ser
            195             200             205

Leu Ser Asp Tyr Glu Glu Asp Met Gln Gln Met Lys Asn Leu Gly Lys
        210             215             220

Glu Glu Phe Val His Leu Leu Arg Arg His Ser Thr Gly Phe Ser Arg
225             230             235             240

Gly Ser Ser Lys Phe Arg Gly Val Thr Leu His Lys Cys Gly Arg Trp
            245             250             255

Glu Ala Arg Met Gly Gln Phe Leu Gly Lys Lys Tyr Ile Tyr Leu Gly
            260             265             270

Leu Phe Asp Ser Glu Val Glu Ala Ala Arg Ala Tyr Asp Lys Ala Ala
            275             280             285

Ile Lys Thr Ser Gly Arg Glu Ala Val Thr Asn Phe Glu Pro Ser Ser
        290             295             300

Tyr Glu Gly Glu Thr Met Ser Leu Pro Gln Ser Glu Gly Ser Gln His
305             310             315             320

Asp Leu Asp Leu Asn Leu Gly Ile Ser Thr Thr Ser Ser Lys Glu Asn
            325             330             335

Asp Arg Leu Gly Gly Ser Arg Tyr His Pro Tyr Asp Met Gln Asp Ala
            340             345             350

Thr Lys Pro Lys Met Asp Lys Pro Gly Ser Val Ile Val Gly Ser Ser
        355             360             365

His Leu Lys Gly Leu Ser Met Ser Ser Gln Gln Ala Gln Leu Trp Thr
    370             375             380

Gly Ile Tyr Ser Asn Phe Ser Ser Ser Tyr Glu Gly Arg Ala Tyr Asp
385             390             395             400

Lys Arg Lys Asp Thr Gly Ser Ser Gln Gly Pro Pro Asn Trp Ala Leu
            405             410             415

Gln Met Pro Ser Gln Val Asp Thr Asn Ser Pro Leu Thr Met Phe Cys
            420             425             430

Thr Ala Ser Ser Ser Gly Phe Phe Ile Pro Ser Thr Thr Ser Val Thr
            435             440             445
```

-continued

```
Ser Ser Thr Ser Ala Leu Ala Thr Ser Thr Asn Ala Ser Gln Cys Phe
    450                 455                 460

Tyr Gln Ile Asn Pro Arg Leu Pro Leu Pro
465                 470

<210> SEQ ID NO 7
<211> LENGTH: 28
<212> TYPE: DNA
<213> ORGANISM: Artificial Sequence
<220> FEATURE:
<223> OTHER INFORMATION: M5 forward

<400> SEQUENCE: 7
gcgaggcatt tgttgaagtt gctaatgc                                          28

<210> SEQ ID NO 8
<211> LENGTH: 22
<212> TYPE: DNA
<213> ORGANISM: Artificial Sequence
<220> FEATURE:
<223> OTHER INFORMATION: M5 reverse

<400> SEQUENCE: 8
ggttgataca aacagcccat tg                                                22

<210> SEQ ID NO 9
<211> LENGTH: 22
<212> TYPE: DNA
<213> ORGANISM: Artificial Sequence
<220> FEATURE:
<223> OTHER INFORMATION: M8 forward

<400> SEQUENCE: 9
aagcaatgcg aaatatcgta ac                                                22

<210> SEQ ID NO 10
<211> LENGTH: 21
<212> TYPE: DNA
<213> ORGANISM: Artificial Sequence
<220> FEATURE:
<223> OTHER INFORMATION: M8 reverse

<400> SEQUENCE: 10
gagagaccct cacattttgt c                                                 21
```